US007425337B2

(12) United States Patent
Smith et al.

(10) Patent No.: US 7,425,337 B2
(45) Date of Patent: Sep. 16, 2008

(54) ALPHAVIRUS REPLICON VECTOR SYSTEMS

(75) Inventors: Jonathan F. Smith, Cary, NC (US);
Kurt I. Kamrud, Apex, NC (US);
Jonathan O. Rayner, Apex, NC (US);
Sergey A. Dryga, Chapel Hill, NC (US);
Ian J. Caley, Durham, NC (US)

(73) Assignee: AlphaVax, Inc., Research Triangle Park, NC (US)

( * ) Notice: Subject to any disclaimer, the term of this patent is extended or adjusted under 35 U.S.C. 154(b) by 0 days.

(21) Appl. No.: 11/376,901

(22) Filed: Mar. 16, 2006

(65) Prior Publication Data

US 2006/0177819 A1    Aug. 10, 2006

Related U.S. Application Data

(62) Division of application No. 10/237,302, filed on Sep. 6, 2002, now Pat. No. 7,045,335.

(60) Provisional application No. 60/317,722, filed on Sep. 6, 2001.

(51) Int. Cl.
*A61K 39/12* (2006.01)
*C12N 15/64* (2006.01)
*C12N 5/02* (2006.01)

(52) U.S. Cl. .................. 424/218.1; 435/325; 435/91.42

(58) Field of Classification Search ................. None
See application file for complete search history.

(56) References Cited

U.S. PATENT DOCUMENTS

| | | |
|---|---|---|
| 4,650,764 A | 3/1987 | Temin |
| 4,708,871 A | 11/1987 | Geysen |
| 5,091,309 A | 2/1992 | Schlesinger |
| 5,185,440 A | 2/1993 | Davis ...................... 536/237.2 |
| 5,217,879 A | 6/1993 | Huang |
| 5,505,947 A | 4/1996 | Johnston ................. 424/218.1 |
| 5,521,082 A | 5/1996 | Lewis et al. |
| 5,639,650 A | 6/1997 | Johnston ..................... 435/236 |
| 5,643,576 A | 7/1997 | Johnston ................. 424/199.1 |
| 5,703,057 A | 12/1997 | Johnston et al. |
| 5,726,022 A | 3/1998 | Burmer |
| 5,739,026 A | 4/1998 | Garoff ..................... 435/320.1 |
| 5,766,602 A | 6/1998 | Xiong ..................... 424/218.1 |
| 5,789,245 A | 8/1998 | Dubensky ............... 435/320.1 |
| 5,792,462 A * | 8/1998 | Johnston et al. .......... 424/199.1 |
| 5,811,407 A | 9/1998 | Johnston ..................... 514/44 |
| 5,814,482 A | 9/1998 | Dubensky ................. 435/69.3 |
| 5,827,658 A | 10/1998 | Liang et al. |
| 5,831,016 A | 11/1998 | Wang et al. |
| 5,843,723 A | 12/1998 | Dubensky ................. 435/69.3 |
| 5,853,719 A | 12/1998 | Nair et al. |
| 5,958,738 A | 9/1999 | Lindemann et al. |
| 5,989,553 A | 11/1999 | Johnston et al. |
| 6,008,035 A | 12/1999 | Johnston ................. 435/235.1 |
| 6,015,686 A | 1/2000 | Dubensky ................. 435/69.1 |
| 6,015,694 A | 1/2000 | Dubensky ................. 435/69.3 |
| 6,146,874 A | 11/2000 | Zolotukhin ............... 435/235.1 |
| 6,156,558 A | 12/2000 | Johnston ................. 435/235.1 |
| 6,190,666 B1 | 2/2001 | Garoff ..................... 424/208.1 |
| 6,194,191 B1 | 2/2001 | Zhang et al. |
| 6,197,502 B1 | 3/2001 | Renner et al. |
| 6,224,879 B1 | 5/2001 | Sjoberg ................... 424/218.1 |
| 6,242,259 B1 | 6/2001 | Polo ........................... 435/456 |
| 6,261,570 B1 | 7/2001 | Parker ..................... 424/205.1 |
| 6,267,967 B1 | 7/2001 | Johnston et al. |
| 6,306,388 B1 | 10/2001 | Nair et al. |
| 6,329,201 B1 * | 12/2001 | Polo et al. ................. 435/320.1 |
| 6,342,372 B1 | 1/2002 | Dubensky ................. 435/69.1 |
| 6,376,236 B1 | 4/2002 | Dubensky ................. 435/320.1 |
| 6,391,632 B1 | 5/2002 | Dubensky ................. 435/325 |
| 6,426,196 B1 | 7/2002 | Dubensky et al. |
| 6,485,958 B2 | 11/2002 | Blanche et al. |
| 6,495,143 B2 | 12/2002 | Lee et al. |
| 6,521,235 B2 | 2/2003 | Johnston et al. |
| 6,531,135 B1 | 3/2003 | Johnston et al. |
| 6,541,010 B1 * | 4/2003 | Johnston et al. .......... 424/199.1 |

(Continued)

FOREIGN PATENT DOCUMENTS

| | | |
|---|---|---|
| WO | WO 02/10578 | 6/1992 |
| WO | WO 92/10578 | 6/1992 |
| WO | WO 95/07994 | 3/1995 |
| WO | WO 95/27044 | 10/1995 |
| WO | WO 95/31565 | 11/1995 |
| WO | WO 96/17072 | 6/1996 |
| WO | WO 96/37220 | 11/1996 |
| WO | WO 96/37616 | 11/1996 |
| WO | WO 99/07834 | 2/1999 |
| WO | WO 99/08706 | 2/1999 |
| WO | WO 99/51263 | 10/1999 |
| WO | WO 00/39302 | 7/2000 |
| WO | WO 00/39318 | 7/2000 |
| WO | WO 00/61772 | 10/2000 |
| WO | WO 01/16343 | 3/2001 |

(Continued)

OTHER PUBLICATIONS

Lemm et al., Assembly of Functional Sindbis Virus RNA Replication Complexes: Requirement for Coexpression of P123 and P34, .1993, Journal of Virology, vol. 67, No. 4, pp. 1905-1915.*

(Continued)

*Primary Examiner*—Bruce Campell
*Assistant Examiner*—Benjamin P Blumel
(74) *Attorney, Agent, or Firm*—Myers Bigel Sibley & Sajovec, P.A.

(57) ABSTRACT

The present invention provides compositions useful in and methods for producing populations of infectious, replication-defective alphavirus replicon particles that contain no replication competent alphavirus particles, as determined by passage on cells in culture. The compositions include helper and replicon nucleic acid molecules that can further reduce the predicted frequency for formation of replication-competent virus and can optimize manufacturing strategies and costs.

34 Claims, No Drawings

U.S. PATENT DOCUMENTS

| | | | |
|---|---|---|---|
| 6,583,121 | B1 | 6/2003 | Johnston et al. |
| 6,767,699 | B2 | 7/2004 | Polo et al. |
| 6,770,283 | B1 | 8/2004 | Garoff et al. |
| 6,783,939 | B2 | 8/2004 | Olmsted et al. |
| 6,844,188 | B1 | 1/2005 | MacDonald et al. |
| 7,045,335 | B2* | 5/2006 | Smith et al. .............. 435/235.1 |
| 7,235,235 | B2* | 6/2007 | Johnston et al. ............ 424/93.2 |
| 2001/0016199 | A1 | 8/2001 | Johnston et al. |
| 2002/0018766 | A1 | 2/2002 | Roberts et al. |
| 2002/0034521 | A1 | 3/2002 | Lee et al. |
| 2002/0102273 | A1 | 8/2002 | Grieve et al. |
| 2002/0141975 | A1 | 10/2002 | Olmsted et al. |
| 2002/0164582 | A1 | 11/2002 | Hart et al. |
| 2003/0021766 | A1 | 1/2003 | Vadjy et al. |
| 2003/0091591 | A1 | 5/2003 | Xiong et al. |
| 2003/0096397 | A1 | 5/2003 | Schlesinger et al. |
| 2003/0119182 | A1 | 6/2003 | Smith et al. |
| 2003/0120060 | A1 | 6/2003 | Gonczol et al. |
| 2003/0148262 | A1* | 8/2003 | Polo et al. ..................... 435/5 |
| 2003/0152590 | A1 | 8/2003 | Hevey et al. |
| 2003/0232036 | A1 | 12/2003 | Johnston et al. |
| 2003/0232324 | A1 | 12/2003 | Polo et al. |
| 2004/0009183 | A1 | 1/2004 | Lee et al. |
| 2004/0009945 | A1 | 1/2004 | Lee et al. |
| 2004/0029279 | A1 | 2/2004 | Kovacs et al. |
| 2004/0030117 | A1 | 2/2004 | Johnston et al. |
| 2004/0121466 | A1 | 6/2004 | Johnston et al. |
| 2004/0146859 | A1 | 7/2004 | Hart et al. |
| 2004/0166573 | A1 | 8/2004 | Smith et al. |
| 2004/0208848 | A1 | 10/2004 | Smith et al. |
| 2005/0031592 | A1 | 2/2005 | Doolan et al. |
| 2005/0054107 | A1 | 3/2005 | Chulay et al. |
| 2005/0118251 | A1 | 6/2005 | Nagata et al. |

FOREIGN PATENT DOCUMENTS

| | | |
|---|---|---|
| WO | WO 02/003917 | 1/2002 |
| WO | WO 02/04493 | 1/2002 |
| WO | WO 02/20721 | 3/2002 |
| WO | WO 03/023026 A | 3/2003 |
| WO | WO 03/083065 | 10/2003 |
| WO | WO 04/055166 | 7/2004 |
| WO | WO 04/055167 | 7/2004 |
| WO | WO 04/085660 | 10/2004 |
| WO | WO 05/007689 | 1/2005 |

OTHER PUBLICATIONS

Documents from the Opposition filed by Chiron Corporation in the Australian Patent Office against the grant of Australian Patent No. 727036 (Australian Application Serial No. 59256/96) including (i) Notice of Opposition filed by Chiron Corporation dated Feb 28, 2001; (ii) Statement of Grounds of Opposition and Particulars Relating to Each Ground filed by Chiron Corporation dated May 28, 2001; (iii) Evidence-in-Support filed by Chiron Corporation including Statutory Declaration of Nicholas James Finnie dated May 28, 2002 with Exhibits NJF-1 to NJF-13; Statutory Declaration of John Polo dated Aug. 27, 2002 with Exhibits JP-1 to JP-10; and Statutory Declaration of Alexander A. Khromykh dated Oct. 14, 2002 with Exhibits AK-1 to AK-2; (iv) Submission by Chiron Corporation to Commissioner of Patents, Australia dated May 11, 2006 advising that the opposition against the grant of Australian Patent No. 727036 is withdrawn; and (v) Communication issued by IP Australia acknowledging withdrawal of opposition by Chiron Corporation.

Baric et al. "Expression and Self-Assembly of Norwalk Virus Capsid Protein from Venezuelan Equine Encephalitis Virus Replicons", *Journal of Virology* 76(6):3023-3030 (2002).

Davis et al. "Alphavirus Replicon Particles as Candidate HIV Vaccines" *IUBMB Life* 53:209-211 (2002).

Eiben et al. "Establishment of an HLA-A*0201 Human Papillomavirus Type 16 Tumor Model to Determine the Efficacy of Vaccination Strategies in HLA-A*0201 Transgenic Mice" *Cancer Research* 62:5792-5799 (2002).

Eralp et al. "Doxorubicin and Paclitaxel Enhance the Antitumor Efficacy of Vaccines Directed Against HER 2/neu in a Murine Mammary Carcinoma Model" *Breast Cancer Research* 6:R275-R283 (2004).

Gidwitz et al. "Differences in virion stability among Sindbis virus pathogenesis mutants" *Virus Research* 10:225-240 (1988).

Johnston et al. "Selection for Accelerated Penetration in Cell Culture Coselects for Attenuated Mutants of Venezuelan Equine Encephalitis Virus" *Virology* 162:437-443 (1988).

Johnston et al. "Studies of Alphavirus Virulence Using Full-Length Clones of Sindbis and Venezuelan Equine Encephalitis Viruses" M.A. Brinton et al. (eds), *New Aspects of Positive Strand RNA Viruses*, pp. 334-339 ASM Press, (1990).

Kaufman et al. "Improved vectors for stable expression of foreign genes in mammalian cells by use of the untranslated leader sequence from EMC virus" *Nucleic Acids Research* 19(16):4485-4490 (1991).

Khromyck "Replicon-based vectors of positive strand RNA viruses" *Current Opinion in Molecular Therapeutics* 2(5):555-569 (2000).

Lee et al. "Candidate Vaccine Against Botulinum Neurotoxin Serotype A Derived from a Venezuelan Equine Encephalitis Virus Vector System" *Infection and Immunity* 69(9):5709-5715 (2001).

Lee et al. "Immune Protection Against Staphylococcal Enterotoxin-Induced Toxic Shock by Vaccination with a Venezuelan Equine Encephalitis Virus Replicon" *Journal of Infectious Diseases* 185:1192-1196 (2002).

MacDonald et al. "Rols of Dendritic Cell Targeting in Venezuelan Equine Encephalitis Virus Pathogenesis" *Journal of Virology* 74(2):914-922 (2000).

Nelson et al. "Venezuelan Equine Encephalitis Replicon Immunization Overcomes Intrinsic Tolerance and Elicits Effective Anti-Tumor Immunity to the "self" Tumor-Associated Antigen, *neu* in a Rat Mammary Tumor Model" *Breast Cancer Research and Treatment* 82:169-183 (2003).

Olmsted et al. "Sindbis Virus Mutants Selected for Rapid Growth in Cell Culture Display Attenuated Virulence in Animals" *Science* 225(4660):424-427 (1984).

Polo et al. "A Model for In Vitro Development of Live, Recombinant Alphavirus Vaccines", *Vaccines 90: Modern Approaches to New Vaccines Including Prevention of AIDS*, 105-108 Brown et al. (eds) (Cold Spring Harbor Laboratory) (1990).

Polo et al. "Mutational Analysis of Virulence Locus in the E2 Glycoprotein Gene of Sindbis Virus" *Journal of Virology* 65(11):6358-6361 (1991).

Product Descriptions (2), ATCC CRL-11268 and ATCC CRL 12203 [retrieved on Apr 29, 2005]. Retrieved from the Internet >URL: http://www.atcc.org/catalog/numSearch/numResults.cfm>.

Pushko et al. "Individual and Bivalent Vaccines Based on Alphavirus Replicons Protect Guinea Pigs Against Infection with Lassa and Ebola Viruses" *Journal of Virology* 75(23):11677-11685 (2001).

Schultz-Cherry et al. "Influenza Virus (A/HK/156/97) Hemagglutinin Expressed by an Alphavirus Replicon System Protects Chickens Against Lethal Infection with Hong Kong-Origin H5N1 Viruses" *Virology* 278:55-59 (2000).

Wang et al. "Alphavirus Replicon Particles Containing the Gene for HER2/neu Inhibit Breast Cancer Growth and Tumorigenesis" *Breast Cancer Research* 7(1):R145-R155 (2005).

Wilson et al. "Protection from Ebola Virus Mediated by Cytotoxic T Lymphocytes Specific for the Viral Nucleoprotein" *Journal of Virology* 75:(6):2660-2664 (2001).

Balasuriya et al. "Alphavirus Replicon Particles Expressing the Two Major Envelope Proteins of Equine Arteritis Virus Induce High Level Protection Against Challenge with Virulent Virus in Vaccinated Horses" *Vaccine* 20:1609-1617 (2002).

Barry et al. "Expression Library Immunization to Discover and Improve Vaccine Antigens" *Immunological Reviews* 199:68-83 (2004).

Bell et al., "Effect of Low NaCI Medium on the Envelope Glycoproteins of Sindbis Virus" *Journal of Virology* 25(3):764-769 (1978).

Bergman et al. "Long-Term Survival or Dogs with Advanced Malignant Melanoma after DNA Vaccination with Xenogeneic Human Tyrosinase: A Phase I Trial" *Clin. Cancer Research* 9:1284-1290 (2003).

Bernard et al. "Mutations in the E2 Glycoprotein of Venezuelan Equine Encephalitis Virus Confer Heparan Sulfate Interaction, Low Morbidity, and Rapid Clearance from Blood of Mice" *Virology* 276:93-103 (2000).

Casimiro et al. "Vaccine-Induced Immune Responses in Rodents and Nonhuman Primates by Use of a Humanized Immunodeficiency Virus Type I pol Gene" *Journal of Virology* 76:185-195 (2002).

Davis et al. "A Single Nucleotide Change in the E2 Glycoprotein Gene of Sindbid Virus Affects Penetration Rate in Cell Culture and Virulence in Neonatal Mice" *Proc. Natl. Acad. Sci. USA* 83:6771-6775 (1986).

Geisbert et al. "Evaluation in Nonhuman Primates of Vaccines Against Ebola Virus" *Emerging Infect. Dis*. 8(5): 503-507 (2002).
Golzio et al. "Cell Synchronization Effect on Mammalian Cell Permeabilization and Gene Delivery by Electronic Field" *Biochim. Biophys. Acta* 1563:23-28 (2002).
Gonczol and Plotkin "Development of a Cytomegalovirus Vaccine: Lessons from Recent Clinical Trials" *Exp. Opin. Biol. Ther*. 1(3):401-412 (2001).
Hahn et al. "Infectious Sindbis Virus Transient Expression Vectors for Studying Antigen Processing and Presentation" *Proc. Natl. Acad. Sci. USA* 89:2679-2683 (1992).
Hariharan et al. "DNA Immunization Against *Herpes simplex* Virus: Enhanced Efficacy Using a Sindbis Virus-Based Vector" *Journal of Virology* 72(2):950-958 (1998).
Heiser et al. "Autologous Dendritic. Cells Transfected with Prostate-Specific Antigen RNA Stimulate CTL Responses Against Metastatic Prostate Tumors" *J. Clinical Inv*. 109(3): 409-417 (2002).
Hevey et al. "Marburg Virus Vaccines Based upon Alphavirus Replicons Protect Guinea Pigs and Nonhuman Primates" *Virology* 251:28-37 (1998).
Hill et al. "RNA-RNA Recombination in Sindbis Virus: Roles of the 3' Conserved Motif, Poly (A) Tail, and Nonviral Sequences of Template RNAs in Polymerase Recognition and Template Switching" *Journal of /Virology* 71:2693-2704 (1997).
International Search Report issued for PCT/2004/021772; mailed on Dec. 28, 2004.
International Search Report issued for PCT/US03/39723; mailed on Aug. 17, 2004.
International Search Report issued for PCT/US03/39725; mailed on Dec. 3, 2004.
Klimstra et al. "Adaptation of Sindbis Virus to BHK Cells Selects for Use of Heparan Sulfate as an Attachment Receptor" *Journal of Virology* 72:7357-7366 (1998).
Koller et al. "A High-Throughput Alphavirus-Based Expression Cloning System for Mammalian Cells" *Nature Biotech*. 19:851-855 (2000).
Kumamoto et al. "Induction of Tumor-Specific Protective Immunity by in situ Langerhans Cell Vaccine" *Nature Biotech*. 20:64-69 (2002).
Leitner et al. "Enhancement of Tumor-Specific Immune Response with Plasmid DNA Replicon Vectors" *Cancer Research* 60:51-55 (2000).
Li et al. "Production of Infectious Recombinant Moloney Murine Leukemia Virus Particles in BHK Cells using semliki Forest Virus-Derived RNA Expression Vectors" *Proc. Natl. Acad. Sci. USA* 93:11658-11663 (1996).
Liljestrom et al. "In Vitro Mutagenesis of a Full-Length cDNA Clone of Semliki Virus Release" *Journal of Virology* 65:4107-4113 (1991).
Lu et al. "Transmission of Replication-Defective Sindbis Helper Vectors Encoding Capsid and Envelope Proteins" Journal of Virology Methods 91(1):59-65 (2001).
Lundstrom "Alphavirus Vectors: Applications for DNA Vaccine Production and Gene Expression" *Intervirology* 43:247-257 (2000).
McCue and Anders "Soluble Expression and Complex Formation of Proteins Required for HCMV DNA Replication Using the SFV Expression System" *Protein Expression and Purification* 13:301-312 (1998).
Olmsted et al. "Characterization of Sindbis Virus Epitopes Important for Penetration in Cell Culture and Pathogenesis in Animals" *Virology* 148:245-254 (1986).
Overwijk et al. "Creating Therapeutic Cancer Vaccines: Notes from the Battlefield" *Trends in Immunol*. 22(1):5-7 (2001).
Pardoll "Cancer Vaccines" Nature Medicine Vaccine Supplement 4(5):525-531 (1998).
Pardoll "Spinning Molecular Immunology into Successful Immunotherapy" *Nature Reviews—Immunology* 2:227-238 (2002).
Polo et al. "Stable Alphavirus Packaging Cell Lines for Sindbis Virus and Semliki Forest Virus-Deprived Vectors" *Proc. Natl. Acad. Sci*. 96:4598-4603 (1999).
Ragupathi et al. "The Case for Polyvalent Cancer Vaccines that Induce Antibodies" *Expert Rev. Vaccines* 1(2):193-206 (2002).
Sadanaga et al. "Dendritic Cell Vaccination with MAGE Peptide is a Novel Therapeutic Approach for Gastrointestinal Carcinomas" *Clin Cancer Research* 7:2277-2284 (2001).
Schlesinger and Dubensky Jr. "Alphavirus Vectors for Gene Expression and Vaccines" *Current Opinion in Biotechnology* 10(5): 434-439 (1999).
Slepushkin et al. "Large Scale Purification of a Lentiviral Vector by Size Exclusion Chromatography or Mustang Q Ion Exchange Capsule" *Bioprocessing Journal* 89-94 (Sep.-Oct. 2003).
Technical Bulletin No. 166: RiboMAX Large Scale RNA Production Systems—SP6 and T7; Promega Corporation p. 1-11; Revised Sep. 2001; http://www.promega.com/tbs/tb166.pdf on Nov. 4, 2004.
Temperton "DNA Vaccines Against Cytomegalovirus: Current Progress" *International Journal of Antimicrobial Agents* 19:169-172 (2002).
Waite et al. "Inhibition of Sindbis Virus Production by Media of Low Ionic Strength: Intracellular Events and Requirements for Reversal" *Journal of Virology* 5:60-71 (1970).
Ward et al. "Immunotherapeutic Potential of Whole Tumor Cells" *Cancer Immunol. Immunother*. 51:351-357 (2002).
Wilson et al. "Vaccine Potential of Ebola Virus VP24, VP30, VP35 and VP40 Proteins" *Virology* 286:384-390 (2001).
Yamanaka et al. "Enhancement of Antitumor Immune Response in Glioma Models in Mice by Genetically Modified Dendritic Cells Pulsed with Semliki Forest Virus-Mediated Complementay DNA" J. Neurosurgery 94:474-481 (2001).
Yamanaka et al. "Marked Enhancement of Antitumor Immune Responses in Mouse Brain Tumor Models by Genetically Modified Dendritic Cells Producing Semliki Forest Virus-Mediated Interleukin-12" J. Neurosurgery 97:611-618 (2002).
Ying et al. "Cancer Therapy Using a Self-Replicating RNA Vaccine" *Nature Medicine* 5(7):823-827 (1999).
Caley et al., "Venezuelan Equine Encephalitis Virus Vectors Expressing HIV-1 proteins: Vector Design Strategies for Improved Vaccine Efficacy," *Vaccine*, 17 3124-3135 (1999).
Li et al., "Production of Infectious Recombinant Moloney Murine Leukemia Virus Particles in BHK Cells Using Semliki Forest Virus-Derived RNA Expression Vectors," *Proc. Natl. Acad. Sci. USA*, 93 11658-11663 (Oct. 1996).
Chulay et al. "Alphavirus-based Cytomegalovirus Vaccines" U.S. Appl. No. 10/886,773, filed in the U.S. Patent and Trademark Office on Jul. 8, 2004.
International Search Report corresponding to PCT/US2004/008458, mailed on Oct. 25, 2004.
Knight "Secretion from Bovine Chromaffin Cells Acutely Expressing Exogenous Proteins using a Recombinant Semliki Forest Virus Containing an EGFP Reporter" *Molecular and Cellular Neuroscience* 14(6):486-505 (1999).
Kohl et al. "Transient Gene Expression in Mammalian and Mosquito Cells Using a Recombinant Semliki Forest Virus Expressing T7 RNA Polymerase" *Applied Microbiology and Biotechnology* 53(1):51-56 (1999).
Olmsted et al. "Alphavirus Vectors and Virosomes with Modified HIV Genes for Use in Vaccines" U.S. Appl. No. 10/929,234, filed in the U.S. Patent and Trademark Office on Aug. 30, 2004.
Pugachev et al. "Development of a Rubella Virus Vaccine Expression Vector: Use of a Picornavirus Internal Ribosome Entry Site Increases Stability of Expression" *Journal of Virology* 74:10811-10815 (2000).

Rayner et al. "Alphavirus Vectors and Vaccination" *Reviews in Medical Virology* 12(5):279-296 (2002).

Shi et al. "Construction and Characterization of Subgenomic Replicons of New York Strain of West Nile Virus" *Virology* 296(2):219-233 (2002).

Smith et al. "Improved Alphavirus Replicons and Helper Constructs" U.S. Appl. No. 10/804,331, filed in the U.S. Patent and Trademark Office on Mar. 19, 2004.

Wang et al. "Core Protein-Coding Sequence, But Not Core Protein, Modulates the Efficiency of Cap-Independent Translation Directed by the Internal Ribosome Entry Site of Hepatitis C Virus" *Journal of Virology* 74(23):11347-11358 (2000).

Wen et al. "Tricistronic Viral Vectors Co-Expressing Interleukin-12 (IL-12) and CD80 (B7-1) for the Immunotherapy of Cancer: Preclinical Studies in Myeloma" *Cancer Gene Therapy* 8(5):361-370 (2001).

Wilson et al. "Naturally Occurring Dicistronic Cricket Paralysis Virus RNA is Regulated by Two Internal Ribosome Entry Sites" *Molecular and Cellular Biology* 20(14):4990-4999 (2000).

Anu Jalanko. 1985. Expression of Semliki Forest Virus Capsid Protein from SV40 Recombinant Virus. *FEBS Letters* 186:59-64.

Berglund et al. 1993. Semliki Forest Virus Expression System: Production of Conditionally Infectious Recombinant Particles, *Bio/Technology* 11:916-920.

Betts et al. 1997. Cross-Clade Human Immunodeficiency Virus (HIV)-Specific Cytotoxic T-Lymphocyte Responses in HIV-Infected Zambians. *J. Virol.* 71(11):8908-8911.

Bredenbeek et al. 1993. Sindbis Virus Expression Vectors: Packaging of RNA Replicons by Using Defective Helper RNAs. *Journal of Virology* 67:6439-6446.

Caley et al. 1997. Humoral, Mucosal, and Cellular Immunity in Response to a Human Immunodeficiency Virus Type 1 Immunogen Expressed by a Venezuelan Equine Encephalitis Virus Vaccine Vector. *J. Virol.* 71(4):3031-3038.

Corsini et al. 1996. Efficiency of Transduction by Recombinant Sindbis Replicon Virus Varies Among Cell Lines, Including Mosquito Cells and Rat Sensory Neurons. *BioTechniques* 21(3):492-497.

Cutler et al. 1986. Mutants of the Membrane-binding Region of Semliki Forest Virus E2 Protein. I. Cell Surface Transport and Fusogenic Activity. *The Journal of Cell Biology* 102: 889-901.

Davis et al. 1993. A Genetically Engineered Live Virus Vaccine for Venezuelan Equine Encephalitis. *J. Cell Biochemistry* Supplement O No. 17 Part D, Abstract N404.

Davis et al. 1996. A Viral Vaccine Vector that Expresses Foreign Genes in Lymph Nodes and Protects against Mucosal Challenge. *Journal of Virology* 70: 3781-3787.

Davis et al. 1995. Attenuated Mutants of Venezuelan Equine Encephalitis Virus Containing Lethal Mutations in the PE2 Cleavage Signal Combined with a Second-Site Suppressor Mutation in E1. *Virology* 212:102-110.

Davis et al. 1991. Attenuating Mutations in the E2 Glycoprotein Gene of Venezuelan Equine Encephalitis Virus: Construction of Single and Multiple Mutants in a Full-Length cDNA Clone. *Virology* 183:20-31.

Davis et al. 1996. Immunization against Influenza with Attenuated Venezuelan Equine Encephalitis Virus Vectors. In: *Options for the Control of Influenza III*. L. E. Brown and A. W. Hampson, eds. Elsevier, Amsterdam pp. 803-809.

Davis et al. 1990. In Vitro Synthesis of Infectious Venezuelan Equine Encephalitis Virus RNA from a cDNA Clone: Analysis of a Viable Deletion Mutant and Mutations Affecting Virulence. *Vaccines* 90:109-113.

Davis et al. 1989. In Vitro Synthesis of Infectious Venezuelan Equine Encephalitis Virus RNA from a cDNA Clone: Analysis of A Viable Deletion Mutant. *Virology* 171:189-204.

Davis et al. 2001. Vaccination of Macaques against Pathogenic Simian Immunodeficiency Virus with Venezuelan Equine Encephalitis Virus Replicon Particles. *J. Virol.* 74(1):371-378.

Davis et al. 1994. A molecular genetic approach to the study of Venezuelan equine encephalitis virus pathogenesis. *Archives of Virology* 9:99-109.

Dubensky et al. 1996 Sindbis Virus DNA-Based Expression Vectors: Utility for in Vitro and in Vivo Gene Transfer. *Journal of Virology* 70:508-519.

Dubuisson et al. 1993. Sindbis Virus Attachment: Isolation and Characterization of Mutants with Impaired Binding to Vertebrate Cells. *Journal of Virology* 67: 3363-3374.

Favre et al. 1993. Semliki Forest Virus Capsid Protein Expressed by a Baculovirus Recombinant. *Archives of Virology* 132:307-319.

Frolov et al. 1996. Alphavirus-based expression vectors: Stategies and applications. *Proc. Natl. Acad. Sci. USA* 93:11371-11377.

Garoff et al. 1983. Expression of Semliki Forest Virus Proteins from Cloned Complementary DNA. II. The Membrane-spanning Glycoprotein E2 is Transported to the Cell Surface without its Normal Cytoplasmic Domain. *The Journal of Cell Biology* 97: 652-658.

Grieder et al. 1995. Specific Restrictions in the Progression of Venezuelan Equine Encephalitis Virus-Induced Disease Resulting from Single Amino Acid Changes in the Glycoproteins. *Virology* 206:994-1006.

Heidner et al. 1994. Lethality of PE2 Incorporation into Sindbis Virus can be Suppressed by Second-Site Mutations in E3 and E2. *Journal of Virology* 68:2683-2692.

Hevey et al. 2002. Marburg Virus Vaccines: Comparing Classical and New Approaches. *Vaccines* 20:586-593.

Hirsch et al. 1996. Patterns of Viral Replication Correlate with Outcome in Simian Immunodeficiency Virus (SIV)-Infected Macaques: Effects of Prior Immunization with a Trivalent SIV Vaccine in Modified Vaccinia Virus Ankara. *J. Virol.* 70(6):3741-3752.

Hodgson et al. 1993. Expression of Venezuelan Equine Encephalitis Virus Proteins by Recombinant Baculoviruses. *The American Journal of Tropical Medicine and Hygiene*. 49:195-196 (Supplement).

Polo and Johnston. 1990. Attenuating Mutations in Glycoproteins E1 and E2 of Sindbis Virus Produce a Highly Attenuated Strain When Combined in Vitro. *Journal of Virology* 64:4438-4444.

Johnston and Peters. 1996. Alphaviruses. *In: Fields Virology*, 3$^{rd}$ ed., Lippincott-Raven Publishers, Philadelphia, Chapt, 28:843-898.

Johnston and Smith. 1988. Selection for Accelerated Penetration in Cell Culture Coselects for Attenuated Mutants of Venezuelan Equine Encephalitis Virus. *Virology* 162:437-443.

Kinney et al. 1989. The Full-Length Nucleotide Sequences of the Virulent Trinidad Donkey Strain of Venezuelan Equine Encephalitis Virus and its Attenuated Vaccine Derivative, Strain TC-83. *Virology* 170:19-30.

Kinney et al. 1993. Attenuation of Venezuelan Equine Encephalitis Virus Strain TC-83 Is Encoded by the 5'-Noncoding Region and the E2 Envelope Glycoprotein. *Journal of Virology* 67:1269-1277.

Lemm et al. 1994. Polypeptide requirements for assembly of functional Sindbis virus replication complexes: a model for the temporal regulation of minus- and plus-strand RNA synthesis. *The EMBO Journal* 13:2925-2934.

Liljestrom et al. 1991. A New Generation of Animal Cell Expression Vectors Based on the Semliki Forest Virus Replicon, *Bio/Technology* 9:1356-1361.

Liljeström. 1994. Alphavirus expression systems. *Current Opinion in Biotechnology* 5:495-500.

Lobigs et al. 1990. Fusion Function of the Semliki Forest Virus Spike is Activated by Proteolytic Cleavage of the Envelope Glycoprotein Precursor p62. *Journal of Virology* 64: 1233-1240.

Lundström et al. 1985. Secretion of Semliki Forest Virus Membrane Glycoprotein E1 from *Bacillus subtilis* Virus Research 2:69-83.

Melancon et al. 1987. Processing of the Semliki Forest Virus Structural Polyprotein: Role of the Capsid Protease. *Journal of Virology* 61:1301-1309.

Melancon et al. 1986. Reinitiation of Translocation in the Semliki Forest Virus Structural Polyprotein: Identification of the Signal for the E1 Glycoprotein. *The EMBO Journal* 5:1551-1560.

Morgenstern et al. 1990. Advanced mammalian gene transfer: high titre retroviral vectors with multiple drug selection markers and a complementary helper-free packaging cell line. *Nucleic Acids Research* 18:3587-3596.

Paredes et al. 1993. Three-dimensional Structure of a Membrane-Containing Virus. *Proc. Natl. Acad. Sci. USA* 90:9095-9099.

Presley et al. 1991. Proteolytic Processing of the Sindbis Virus Membrane Protein Precursor PE2 is Nonessential for Growth in Vertebrate Cells but is Required for Efficient Growth in Invertebrate Cells. *Journal of Virology* 65:1905-1909.

Pushko et al. 1997. Replicon-Helper Systems from Attenuated Venezuelan Equine Encephalitis Virus: Expression of Heterologous Genes in Vitro and Immunization Against Heterologous Pathogens in Vivo. *Virology* 239: 389-401.

Riedel. 1985. Different Membrane Anchors Allow the Semliki Forest Virus Spike Subunit E2 to Reach the Cell Surface. *Journal of Virology* 54:224-228.

Russell et al. 1989. Sindbis Virus Mutations Which Coordinately Affect Glycoprotein Processing, Penetration, and Virulence in Mice. *Journal of Virology* 63:1619-1629.

Salminen et al. 1992. Membrane Fusion Process of Semliki Forest Virus II: Cleavage-dependent Reorganization of the Spike Protein Complex Controls Virus Entry. *The Journal of Cell Biology* 116:349-357.

Schlesinger and Schlesinger. 1996. *Togaviridae*: The Viruses and Their Replication. In: *Fields Virology*, 3rd edition. (Fields et al., eds.) Lipincott-Raven Publishers, Philadelphia.

Schlesinger and Weiss. 1994. Recombination between Sindbis virus RNAs. *J. Virol*. 65:4017-4025.

Schoepp and Johnston. 1993. Directed Mutagenesis of a Sindbis Virus Pathogenesis Site. *Virology* 193:149-159.

Simpson et al. 1996. Complete Nucleotide Sequence and Full-Length cDNA Clone of S.A.AR86, a South African Alphavirus Related to Sindbis. *Virology* 222:464-469.

Sjöberg, et al. 1994. A Significantly Improved Semliki Forest Virus Expression System Based on Translation Enhancer Segments from the Viral Capsid Gene. *Bio/Technology* 12:1127-1131.

Smerdou and Liljestrom. 1999. Two-Helper RNA System for Production of Recombinant Semliki Forest Virus Particles. *Journal of Virology* 73(2):1092-1098.

Schlesinger. 1993. Alphaviruses—vectors for the expression of heterologous genes. *TiBTech* 11:18-22.

Strauss et al. 1994. The Alphaviruses: Gene Expression, Replication, and Evolution. *Microbiological Reviews* 58:491-562.

Suomalainen et al. 1992. Spike Protein-Nucleocapsid Interactions Drive the Budding of Alphaviruses. *Journal of Virology* 66(8):4737-4747.

Ubol et al. 1994. Neurovirulent Strains of Alphavirus Induce Apoptosis in bcl-2-expresing Cells: Role of a Single Amino Acid Change in the E2 Glycoprotein. *Proc. National Academy Sciences* 91: 5202-5206.

Wen et al. 1986. Expression of Genes Encoding Vesicular Stomatitis and Sindbis Virus Glycoproteins in Yeast Leads to Formation of Disulfide-Linked Oligomers. *Virology* 153:150-154.

Xiong et al. 1989. Sindbis Virus: An Efficient, Broad Host Range Vector for Gene Expression in Animal Cells. *Science* 243:1188-1191.

Zhao et al. 1992. Role of Cell Surface Spikes in Alphavirus Budding. *Journal of Virology* 66:7089-7095.

Weiss and Schlesinger. 1991. Recombination between Sindbis Virus RNAs. *Journal of Virology* 65: 4017-4025.

Barouch et al. 2000. Augmentation of Immune Responses to HIV-1 and Simian Immunodeficiency Virus DNA Vaccines by IL-2/Ig Plasmid Administration in Rhesus Monkeys. *PNAS* 97(8): 4192-4197.

Feyzi et al. 1997. Structural Requirement of Heparan Sulfate for Interaction with *Herpes simplex* Virus Type 1 Virions and Isolated Glycoprotein C. *The Journal of Biological Chemistry* 272(40):24850-24857.

Herweijer et al. 1997. Self-Amplifying Vectors for Gene Delivery. *Advanced Drug Delivery Reviews* 27:5-16.

Kondor-Koch et al. 1983. Expression of Semliki Forest Virus Proteins from Cloned Complementary DNA. I. The Fusion Activity of the Spike Glycoprotein. *J. Cell Biology* 97(3):644-651.

Lee et al. 1997. Efficient Long-Term Coexpression of a Hammerhead Ribozyme Targeted to the U5 Region of HIV-1 LTR by Linkage to the Multidrug-Resistance Gene. *Antisense & Nucleic Acid Drug Development* 7:511-522.

Leone et al. 1985. In Vitro Synthesis of the Gene Coding for the Glycoprotein E1 of Sindbis Virus. *Microbiologica* 8(2):123-130.

Oker-Blom et al. 1989. Expression of Sindbis Virus 26S cDNA in *Spodoptera frugiperda* (Sf9) Cells, Using a Baculovirus Expression Vector. *J. Virology* 63:1256-1264.

Orkin et al. 1995. Report and Recommendations of the Panel to Assess the NIH Investment in Research on Gene Therapy.

Rice et al. 1985. Expression of Sindbis Virus Structural Proteins via Recombinant Vaccinia Virus: Synthesis, Processing, and Incorporation into Mature Sindbis Virions. *J. Virology* 56:227-239.

Strauss and Strauss. 1990. Alphavirus Proteinases. *Seminars In Virology* 1:347-356.

Sykes and Johnston. 1999. Genetic Live Vaccines Mimic the Antigenicity but Not Pathogenicity of Live Viruses. *DNA and Cell Biology*. 18(7):521-531.

Ute Geigenmuller-Gnirke et al. 1991. Complementation Between Sindbis Viral RNAs Produces Infectious Particles with a Bipartite Genome. *Proceedings of the National Academy of Sciences* 88:3253-3257.

Verma et al. 1997. Gene Therapy—Promises, Problems and Prospects. *Nature* 389:239-242.

International Search Report of International Application Serial No. PCT/US02/28610 filed Sep. 6, 2002.

Bourne et al. "Preconception Immunization with a Cytomegalovirus (CMV) Glycoprotein Vaccine Improves Pregnancy Outcome in a Guinea Pig Model of Congenital CMV Infection" The Journal of Infectious Diseases 183:59-64 (2001).

Carlson et al. "Expression, Purification and Characterization of a Soluble Form of Human Cytomegalovirus Glycoprotein B" Virology 239:198-205 (1997).

Chappell et al. "A 9-nt Segment of a Cellular mRNA can Function as an Internal Ribosome Site (IRES) and when Present in Linked Multiple Copies Greatly Enhances IRES Activity" PNAS 97(4):1536-1541 (2000).

Chatterjee et al. "Modification of Maternal and Congenital Cytomegalovirus Infection by Anti-Glycoprotein B Antibody Transfer in Guinea Pigs" The Journal of Infectious Diseases 183:1547-1553 (2001).

Geysen et al. "Use of Peptide Synthesis to Probe Viral Antigens for Epitopes to a Resolution of a Single Amino Acid" Proceedings of the National Academy of Sciences of the United States of America 81(13):3998-4002(1984).

Geysen et al. "A Priori Delineation of a Peptide which Mimics a Discontinuous Antigenic Determinant" Molecular Immunology 23(7):709-715 (1986).

Gingras et al. "Activation of the Translational Suppressor 4E-BP1 Following Infection with Encephalomyocarditis Virus and Poliovirus" Proc. Natl. Acad. Sci. USA 93:5578-5583 (1996).

Gradi et al. "Proteolysis of Human Eukaryotic Translation Initiation Factor eIF4GII, but Not eIF4GI, Coincides with the Shutoff of Host Protein Synthesis after Poliovirus Infection" Proc. Natl. Acad. Sci. USA 95:11089-11094 (1998).

Gyulai et al. "Cytotoxic T Lymphocyte (CTL) Responses to Human Cytomegalovirus pp65, IE1-Exon4, gB, pp150, and pp28 in Healthy Individuals: Reevaluation of Prevalence of IE1-Specific CTLs" J. Infect. Dis. 181:1537-1546(2000).

Heise et al. "An Attenuating Mutation in nsP1 of the Sindbis-Group Virus S.A.AR86 Accelerates Nonstructural Protein Processing and Up-Regulates Viral 26S RNA Synthesis" Journal of Virology 77(2):1149-1156 (2003).

Holcik and Komeluk "Functional Characterization of the X-Linked Inhibitor of Apoptosis (XIAP) Internal Ribosome Entry Site Element: Role of La Autoantigen in XIAP Translation" Molecular and Cellular Biology 20(13):4648-4657 (2000).

Holcik et al. "A New Internal-Ribosome-Entry-Site Motif Potentiates XIAP-Mediated Cytoprotection" Nature Cell Biology 1:190-192 (1999).

Holcik et al. "The Internal Ribosome Entry Site-Mediated Translation of Antiapoptotic Protein XIAP is Modulated by the Heterogeneous Nuclear Ribonucleoproteins C1 and C2" Molecular and Cellular Biology 23(1):280-288 (2003).

Jang and Wimmer "Cap-Independent Translation of Encephalomyocarditis Virus RNA: Structural Elements of the Internal Ribosomal Entry Site and Involvement of a Cellular 57-kD RNA-Binding Protein" Genes & Development 4:1560-1572 (1990).

Joachims et al. "Cleavage of Poly(A)-Binding Protein by Enterovirus Proteases Concurrent with Inhibition of Translation In Vitro" Journal of Virology 73(1):718-727 (1999).

Maecker et al. "Use of Overlapping Peptide Mixtures as Antigens for Cytokine Flow Cytometry" Journal of Immunological Methods 255:27-40 (2001).

Martinez-Salas et al. "Functional Interactions in Internal Translation Initiation Directed by Viral and Cellular IRES Elements" Journal of General Virology 82:973-984(2001).

McKnight et al. "Deduced Consensus Sequence of Sindbis Virus Strain AR339: Mutations Contained in Laboratory Strains Which Affect Cell Culture and In Vivo Phenotypes" Journal of Virology 70(3):1981-1989 (1996).

Morello et al. "Suppression of Murine Cytomegalovirus (MCMV) Replication with a DNA Vaccine Encoding MCMV M84 (a Homolog of Human Cytomegalovirus pp65)" Journal of Virology 74(8):3696-3708 (2000).

Pedersen et al. "Separation, Isolation, and Immunological Studies of the Structural Proteins of Venezuelan Equine Encephalomyelitis Virus" J. Virology 14(4):740-744 (1974).

Plotkin et al. "Multicenter Trial of Towne Strain Attenuated Virus Vaccine in Seronegative Renal Transplant Recipients" Transplantation 58(11):1176-1178(1994).

Roberts and Belsham "Complementaion of Defective Picornavirus Internal Ribosome Entry Site(IRES) Elements by the Coexpression of Fragments of the IRES" Virology 227:53-62 (1997).

Thompson and Samow "Enterovirus 71 Contains a Type I IRES Element that Functions When Eukaryotic Initiation Factor eIF4G is Cleaved" Virology 315:259-266 (2003).

Van der Velden et al. "Defective Point Mutants of the Encephalomyocarditis Virus Internal Ribosome Entry Site can be Complemented in Trans" Virology 214:82-90 (1995).

Walter et al. "Reconstitution of Cellular Immunity Against Cytomegalovirus in Recipients of Allogeneic Bone Marrow by Transfer of T-Cell Clones from the Donor" The New England Journal of Medicine 333(16):1038-1044 (1995).

Williamson et al. "Characterization and Selection of HIV-1 Subtype C Isolates for Use in Vaccine Development" AIDS Research and Human Retroviruses 19(2):133-144 (2003).

Williamson et al. "Designing HIV-1 Subtype C Vaccines for South Africa" South Africa Journal of Science 96:318-324 (2000).

Yang and Samow "Location of the Internal Ribosome Entry Site in the 5' Non-Coding Region of the Immunoglobulin Heavy-Chain Binding Protein (BiP) mRNA: Evidence for Specific RNA-Protein Interactions" Nucleic Acids Research 25(14):2800-2807 (1997).

Tugizov et al. "Mutated Forms of Human Cytomegalovirus Glycoprotein B Are Impaires in Inducing Syncytium Formation" *Virology* 209:580-591 (1995).

Vaz-Santiago et al. "Ex Vivo Stimulation and Expansion of both CD4+ and CD8+ T Cells from Peripheral Blood Mononuclear Cells of Human Cytomegalovirus-Seropositive Blood Donors by Using a Soluble Recombinant Chimeric Protein, IE1-pp65" *Journal of Virology* 75(17):7840-7847 (2001).

Velders et al. "Eradication of Established Tumors by Vaccination with Venezuelan Equine Encepalitis Virus Replicon Particles Delivering Human Papillomavirus" *Cancer Research* 61:7861-7867 (2001).

* cited by examiner

ALPHAVIRUS REPLICON VECTOR SYSTEMS

CROSS-REFERENCE TO RELATED APPLICATIONS

This application is a divisional application of, and claims priority to, U.S. application Ser. No. 10/237,302, filed Sep. 6, 2002, now U.S. Pat. No. 7,045,335, issued on May 16, 2006, which claims benefit of priority from U.S. Provisional Application No. 60/317,722, filed Sep. 6, 2001, the entire contents of each of which are incorporated by reference herein in their entireties.

FIELD OF THE INVENTION

The present invention relates to improved constructs for and methods of making recombinant alphavirus particles that are useful in immunotherapies for infectious diseases and cancer and in the delivery of genes for therapeutic purposes.

BACKGROUND OF THE INVENTION

Alphaviruses are currently being used as a vector platform to develop vaccines for infectious diseases (e.g. see U.S. Pat. Nos. 5,792,462; 6,156,558; 5,811,407; 5,789,245; 6,015,694; 5,739,026; Pushko et al., *Virology* 239(2): 389-401 (1997), Frolov et al., *J. Virol.* 71(1): 248-258 (1997); Smerdou and Liljestrom, *J. Virol.* 73(2): 1092-1098 (1999). Alphaviruses comprise a genus in the Togaviridae, and members of the genus are found throughout the world, in both vertebrate and invertebrate hosts. Among the most studied alphaviruses for vector platforms are Venezuelan Equine Encephalitis (VEE) Virus, Semiliki Forest Virus (SFV), and Sindbis Virus, the prototype member of the genus. Various constructs have been developed to enhance immunogenicity and effectiveness in vaccine applications. Many of these constructs have also been designed to decrease the likelihood of formation of replication-competent virus through recombination. Johnston et al. (U.S. Pat. Nos. 5,792,462 and 6,156,558, cited above) recognized the potential for recombination from a single helper system (in which the complete set of structural proteins of an alphavirus are on one RNA molecule and the nonstructural proteins and gene of interest are on another molecule), and thus designed "double-helper" systems that utilized two helper RNAs to encode the structural proteins. Dubensky et al. (U.S. Pat. No. 5,789,245) and Polo et al. (U.S. Pat. No. 6,242,259) describe the use of two DNA alphavirus structural protein expression cassettes to package alphavirus replicons or other alphavirus vectors. Liljestrom and colleagues have presented data confirming that a "single helper system" will generate wild-type virus particles through recombination (Bergland, et al. 1993 Biotechnology 11(8): 916-920).

By distributing the viral genes among three nucleic acids, two of which comprise the helper system, as in the above-described art, the theoretical frequency of recombination that would create a replication-competent virus is reduced significantly relative to single helper systems. These existing systems include the use of the alphavirus RNA polymerase recognition signals, so that the helper systems can take advantage of the presence of the alphavirus replication machinery for amplification and efficient expression of helper functions. However, the presence of the terminal recognition signals on the helper RNAs also means that recombinants in which the helper constructs are incorporated into the termini of the replicon RNA by RNA recombination remain replicable. It is also recognized (e.g. Liljestrom et al. U.S. Pat. No. 6,190,666, Column 17, lines 45-48) that the capsid binding region of nsP1 is required for the packaging of alphaviral RNA into virus or viral-like particles, and so removal of this region would result in the reduction of packaging (see also Levis et al. 1986 *Cell* 44:137 and Weiss et al. 1989 *J. Virol.* 63:530).

Thus, in existing replicon systems, known packaging signals are typically included in replicon RNAs and excluded from helper constructs. However, helper RNAs are nonetheless packaged or copackaged at a lower frequency (Lu and Silver (*J. Virol Methods* 2001, 91(1): 59-65), and helper constructs with terminal recognition signals will be amplified and expressed in the presence of a replicon, and potentially yield additional recombination events.

The current preferred dosages for administration of vector replicon particles, as described by Johnston et al., or recombinant alphavirus particles, as described by Dubensky et al., are approximately $10^6$ to $10^8$ particles. In the case of chimpanzee administrations, Dubensky et al. have estimated the need for 4 injections, each containing $10^7$-$10^8$ particles, with a Sindbis-HBV vaccine. Such dosages require large scale manufacturing procedures, and the amounts produced at such scale may be greater than the predicted frequency for the generation of replication-competent viruses in these existing systems.

Thus, there remains a need to further improve systems for manufacturing alphavirus replicon particles to further reduce the predicted frequency for formation of replication-competent virus, and to optimize manufacturing strategies and costs.

SUMMARY OF THE INVENTION

The present invention provides improved alphavirus replicon vector systems for producing infectious, replication defective, alphavirus replicon particles in alphavirus-permissive cells. Encompassed in the invention are improved replicon RNAs and improved helper nucleic acids for expressing the alphavirus structural proteins. During the production of recombinant alphavirus particles, the generation of replication-competent virus particles can occur through recombination alone or through a combination of helper packaging and recombination. Thus, constructs are provided that eliminate or minimize the occurrence of one or both of these events. In addition, these constructs are also designed to minimize the manufacturing complexity and cost of particles made with such constructs. The invention also provides methods of making recombinant alphavirus particles using the claimed constructs, and pharmaceutical compositions comprising these recombinant alphavirus particles.

In a first aspect, resolving DNA helpers are provided, namely recombinant DNA molecules for expressing the alphavirus structural proteins which comprise a promoter directing transcription of RNA from a DNA sequence comprising, in order (i) a first nucleic acid sequence encoding at least one alphavirus structural protein, (ii) a second nucleic acid sequence encoding a ribozyme, (iii) a third nucleic acid sequence encoding an IRES, and (iv) a fourth nucleic acid sequence encoding at least one alphavirus structural protein, wherein at least one alphavirus structural protein encoded by the fourth nucleic acid sequence is not encoded by the first nucleic acid sequence.

In another embodiment of the resolving DNA helpers of this invention, recombinant DNA molecules for expressing alphavirus structural proteins are provided, comprising a promoter directing the transcription of RNA from a DNA sequence comprising, in order: (i) a first nucleic acid sequence encoding a 5' alphavirus replication recognition sequence, (ii) a second nucleic acid sequence encoding either (a) an RNA sequence that promotes transcription of a protein coding RNA sequence or (b) an IRES; (iii) a third nucleic acid sequence encoding at least one alphavirus structural protein, (iv) a fourth nucleic acid sequence encoding a 3' alphavirus replication recognition sequence, (v) a fifth nucleic acid sequence encoding a ribozyme, (vi) a sixth nucleic acid sequence encoding an IRES, and (vii) a seventh nucleic acid sequence encoding at least one alphavirus structural protein, wherein at least one alphavirus structural protein encoded by the seventh nucleic acid sequence is not encoded by the third nucleic acid sequence.

In yet another embodiment of the resolving DNA helpers, the present invention provides a recombinant DNA molecule for expressing alphavirus structural proteins comprising a promoter directing the transcription of RNA from a DNA sequence comprising, in order: (i) a first nucleic acid sequence encoding an IRES, (ii) a second nucleic acid sequence encoding at least one alphavirus structural protein, (iii) a third nucleic acid sequence encoding a ribozyme, (iv) a fourth nucleic acid sequence encoding an IRES, and (v) a fifth nucleic acid sequence encoding at least one alphavirus structural protein, wherein at least one alphavirus structural protein encoded by the fifth nucleic acid sequence is not encoded by the second nucleic acid sequence.

In a second aspect of the invention, methods for producing infectious, replication-defective alphavirus replicon particles comprising introducing into a population of alphavirus-permissive cells one or more resolving DNA helper(s) of the claimed invention and an alphavirus replicon RNA encoding at least one heterologous RNA such that infectious, replication-defective particles are produced.

In a third aspect, the present invention provides resolving RNA helpers, namely recombinant DNA molecules for expressing alphavirus structural proteins comprising: (i) a DNA dependent RNA polymerase promoter, (ii) an IRES, (iii) a nucleic acid sequence encoding an alphavirus capsid protein, which is modified to remove the active site of the autoprotease, (iv) a non-autocatalytic protease recognition site, and (v) a nucleic acid sequence encoding at least one alphavirus glycoprotein.

In another embodiment of the resolving RNA helpers of this invention, a recombinant DNA molecule for expressing a resolving RNA helper in vivo is provided comprising (i) a DNA dependent RNA polymerase promoter, (ii) a nucleic acid sequence encoding at least one alphavirus structural protein, (iii) a non-autocatalytic protease recognition site, and (iv) a nucleic acid sequence encoding at least one alphavirus structural protein, wherein the nucleic acid sequences in (ii) and (iv) are not identical. In preferred embodiments of this aspect, the promoter is an RNA polymerase II promoter that is operable in a helper cell.

In yet another embodiment of the resolving RNA helpers of this invention, a recombinant DNA molecule for expressing an RNA helper in vitro is provided, comprising a promoter directing the transcription of RNA from a DNA sequence comprising (i) a first nucleic acid sequence encoding an alphavirus 5' replication recognition sequence, (ii) a transcriptional promoter, (iii) a nucleic acid sequence encoding at least one alphavirus structural protein, (iv) a non-autocatalytic protease recognition site, and (v) a nucleic acid sequence encoding at least one alphavirus structural protein, and (vi) an alphavirus 3' replication recognition sequence, wherein the nucleic acid sequences of (iii) and (v) are not identical.

In a fourth aspect, methods for producing infectious, replication-defective alphavirus replicon particles comprising introducing into a population of cells (i) one or more resolving RNA helpers of the present invention, (ii) a protease that recognizes the non-autocatalytic protease recognition site, and (iii) an alphavirus replicon RNA encoding at least one heterologous RNA such that infectious, replication-defective alphavirus replicon particles are produced in the cells. In certain embodiments of this aspect, an RNA polymerase that recognizes the DNA dependent RNA polymerase promoter is also made available in the helper cell along with the recombinant DNA molecule, such that the DNA molecule is transcribed in vivo to produce sufficient alphavirus structural proteins for packaging alphavirus replicon particles.

In a fifth aspect of the present invention, a rearranged alphavirus RNA replicon vector is provided comprising in order: (i) a first nucleic acid sequence encoding a 5' alphavirus replication recognition sequence, (ii) a second nucleic acid encoding alphavirus nonstructural proteins nsp1, nsp2, and nsp3; (iii) either (a) a transcriptional promoter or (b) an IRES, (iv) a nucleic acid encoding at least one heterologous gene of interest, (v) an IRES, (vi) a third nucleic acid encoding an alphavirus nonstructural protein nsp4, and (vii) a fourth nucleic acid encoding a 3' alphavirus replication recognition sequence. In another embodiment of this aspect, a vector construct comprising a 5' promoter operably linked to a cDNA of the rearranged alphavirus replicon RNA is provided.

In a sixth aspect, compositions comprising a population of infectious, defective, alphavirus particles, wherein each particle contains an alphavirus replicon RNA comprising a rearranged alphavirus replicon RNA of this invention, and the population has no detectable replication-competent virus, as measured by passage on cell cultures.

In a seventh aspect, a non-replicating DNA helper is provided, namely a recombinant DNA molecule for expressing alphavirus structural proteins comprising a promoter for directing the transcription of RNA from a DNA sequence operably linked to a DNA sequence encoding a complete alphavirus structural polyprotein-coding sequence, with the proviso that the DNA sequence does not encode alphaviral 5' or 3' replication recognition sequences or an alphavirus subgenomic promoter.

In an eighth aspect, a chimeric alphavirus RNA helper is provided, namely a recombinant RNA molecule comprising, in order, a 5' alphavirus replication recognition sequence, a promoter, a nucleic acid encoding at least one alphavirus structural protein, and a 3' alphaviral replication recognition sequence, wherein the promoter is operably linked to the nucleic acid sequence encoding at least one alphavirus structural protein, wherein the transcription-initiating sequence and the RNA polymerase recognition sequence are recognized by the nonstructural viral proteins of Venezuelan equine encephalitis virus, and wherein the transcription-initiating sequence and the RNA polymerase recognition sequence are derived from a virus other than the alphavirus encoding the structural protein.

In a ninth aspect, an alphavirus structural protein expression system based on a virus other than an alphavirus is provided, comprising two RNA molecules, wherein (a) a first RNA encodes sequence for viral replicase proteins, and (b) a second recombinant RNA encodes sequences for (i) the 5' replication recognition sequence for a replication complex comprising the viral replicase proteins of (a), (ii) one or more alphavirus structural proteins, and (iii) the 3' replication recognition sequence for the replication complex comprising the viral replicase proteins of (a), wherein, when the first RNA and the second RNA are introduced into a helper cell, the first RNA replicates the second RNA, then the second RNA is translated to produce one or more alphavirus structural proteins. In preferred embodiments of this aspect, the recombinant RNAs and the viral replicase proteins are derived from a nodavirus.

In a tenth aspect of the invention, methods for producing infectious, replication-defective alphavirus replicon particles comprising introducing into a population of alphavirus-permissive cells one or more helper nucleic acids selected from the group consisting of non-replicating DNA helpers, chimeric alphavirus helpers, and a non-alphavirus based helper system and an alphavirus replicon RNA encoding at least one heterologous RNA, such that the helpers express all of the alphavirus structural proteins, producing said alphavirus replicon particles in the cells, and collecting said alphavirus replicon particles from the cell.

In an eleventh aspect of this invention, helper cells for expressing infectious, replication-defective, alphavirus particles utilizing any combination of the helpers disclosed hereinabove are provided comprising, in an alphavirus-permissive cell, (i) one or more recombinant nucleic acid molecules selected from group consisting of the resolving DNA helpers, the resolving RNA helpers, the non-replicating DNA helpers, the chimeric alphavirus helpers and the non-alphavirus helper system, and (ii) an alphavirus replicon RNA encoding at least one heterologous RNA, wherein the one or more recombinant nucleic acid helpers together encode all alphavirus structural proteins which assemble together into the alphavirus replicon particles.

DETAILED DESCRIPTION OF THE INVENTION

Definitions

As used herein, the term "alphavirus" has its conventional meaning in the art, and includes the various species such as VEE, SFV, Sindbis, Ross River Virus, Western Equine Encephalitis Virus, Eastern Equine Encephalitis Virus, Chikungunya, S.A. AR86, Everglades virus, Mucambo, Barmah Forest Virus, Middelburg Virus, Pixuna Virus, O'nyong-nyong Virus, Getah Virus, Sagiyama Virus, Bebaru Virus, Mayaro Virus, Una Virus, Aura Virus, Whataroa Virus, Banbanki Virus, Kyzylagach Virus, Highlands J Virus, Fort Morgan Virus, Ndumu Virus, and Buggy Creek Virus. The preferred alphaviruses used in the constructs and methods of the claimed invention are VEE, S.AAR86, Sindbis (e.g. TR339, see U.S. Pat. No. 6,008,035), and SFV.

The terms "5' alphavirus replication recognition sequence" and "3' alphavirus replication recognition sequence" refer to the sequences found in alphaviruses, or sequences derived therefrom, that are recognized by the nonstructural alphavirus replicase proteins and lead to replication of viral RNA. These are sometimes referred to as the 5' and 3' ends, or alphavirus 5' and 3' sequences. In the constructs of this invention, the use of these 5' and 3' ends will result in replication of the RNA sequence encoded between the two ends. These sequences can be modified by standard molecular biological techniques to further minimize the potential for recombination or to introduce cloning sites, with the proviso that they must still be recognized by the alphavirus replication machinery.

The term "minimal 5' alphavirus replication recognition sequence" refers to the minimal sequence that allows recognition by the nonstructural proteins of the alphavirus but does not result in significant packaging/recombination of RNA molecules containing the sequence. In a preferred embodiment, the minimal 5' alphavirus replication recognition sequence results in a fifty to one-hundred fold decrease in the observed frequency of packaging/recombination of the RNA containing that sequence. Packaging/recombination of helpers can be assessed by several methods, e.g. the method described by Lu and Silver (*J. Virol Methods* 2001, 91(1): 59-65).

The terms "alphavirus RNA replicon", "alphavirus replicon RNA" and "alphavirus RNA vector replicon" are used interchangeably to refer to an RNA molecule expressing nonstructural protein genes such that it can direct its own replication (amplification) and comprises, at a minimum, the 5' and 3' alphavirus replication recognition sequences, coding sequences for alphavirus nonstructural proteins, and a polyadenylation tract. It may additionally contain a promoter or an IRES. It may also be engineered to express alphavirus structural proteins. Johnston et al. and Polo et al. (cited in the background) describe numerous constructs for such alphavirus RNA replicons, and such constructs are incorporated herein by reference. Specific embodiments of the alphavirus RNA replicons utilized in the claimed invention may contain one or more attenuating mutations, an attenuating mutation being a nucleotide deletion, addition, or substitution of one or more nucleotide(s), or a mutation that comprises rearrangement or chimeric constriction which results in a loss of virulence in a live virus containing the mutation as compared to the appropriate wild-type alphavirus. Examples of an attenuating nucleotide substitution (resulting in an amino acid change in the replicon) include a mutation at nsP1 amino acid position 538, nsP2 amino acid position 96, or nsP2 amino acid position 372 in the alphavirus S.A.AR86.

The terms "alphavirus structural protein/protein(s)" refers to one or a combination of the structural proteins encoded by alphaviruses. These are produced by the virus as a polyprotein and are represented generally in the literature as C-E3-E2-6k-E1. E3 and 6k serve as membrane translocation/transport signals for the two glycoproteins, E2 and E1. Thus, use of the term E1 herein can refer to E1, E3-E1, 6k-E1, or E3-6k-E1, and use of the term E2 herein can refer to E2, E3-E2, 6k-E2, or E3-6k-E2.

The term "helper(s)" refers to a nucleic acid molecule that is capable of expressing one or more alphavirus structural proteins.

The terms "helper cell" and "packaging cell" are used interchangeably herein and refer to the cell in which alphavirus replicon particles are produced. The helper cell comprises a set of helpers that encode one or more alphavirus structural proteins. As disclosed herein, the helpers may be RNA or DNA. The cell can be any cell that is alphavirus-permissive, i.e. cells that are capable of producing alphavirus particles upon introduction of a viral RNA transcript. Alphavirus-permissive cells include, but are not limited to, Vero, baby hamster kidney (BHK), 293, 293T, chicken embryo fibroblast (CEF), and Chinese hamster ovary (CHO) cells. In certain embodiments of the claimed invention, the helper or packaging cell may additionally include a heterologous RNA-dependent RNA polymerase and/or a sequence-specific protease.

The terms "alphavirus replicon particles", "virus replicon particles" or "recombinant alphavirus particles", used interchangeably herein, mean a virion-like structural complex incorporating an alphavirus replicon RNA that expresses one or more heterologous RNA sequences. Typically, the virion-like structural complex includes one or more alphavirus structural proteins embedded in a lipid envelope enclosing a nucleocapsid that in turn encloses the RNA. The lipid envelope is typically derived from the plasma membrane of the cell in which the particles are produced. Preferably, the alphavirus replicon RNA is surrounded by a nucleocapsid structure comprised of the alphavirus capsid protein, and the alphavirus glycoproteins are embedded in the cell-derived lipid envelope. The alphavirus replicon particles are infectious but replication-defective, i.e. the replicon RNA cannot replicate in the host cell in the absence of the helper nucleic acid(s) encoding the alphavirus structural proteins.

As described in detail hereinbelow, the present invention provides improved alphavirus-based replicon systems that reduce the potential for replication-competent virus formation and that are suitable and/or advantageous for commercial-scale manufacture of vaccines or therapeutics comprising them. The present invention provides improved alphavirus RNA replicons and improved helpers for expressing alphavirus structural proteins.

In one embodiment of this invention, a series of "helper constructs", i.e. recombinant DNA molecules that express the alphavirus structural proteins, is disclosed in which a single helper is constructed that will resolve itself into two separate molecules in vivo. Thus, the advantage of using a single helper in terms of ease of manufacturing and efficiency of production is preserved, while the advantages of a bipartite helper system are captured in the absence of employing a bipartite expression system. In one set of these embodiments, a DNA helper construct is used, while in a second set an RNA helper vector is used. In the case of the DNA helper constructs that do not employ alphaviral recognition signals for replication and transcription, the theoretical frequency of recombination is lower than the bipartite RNA helper systems that employ such signals.

In the preferred embodiments for the constructs of this invention, a promoter for directing transcription of RNA from DNA, i.e. a DNA dependent RNA polymerase, is employed. In the RNA helper embodiments, the promoter is utilized to synthesize RNA in an in vitro transcription reaction, and specific promoters suitable for this use include the SP6, T7, and T3 RNA polymerase promoters. In the DNA helper embodiments, the promoter functions within a cell to direct transcription of RNA. Potential promoters for in vivo transcription of the construct include eukaryotic promoters such as RNA polymerase II promoters, RNA polymerase III promoters, or viral promoters such as MMTV and MoSV LTR, SV40 early region, RSV or CMV. Many other suitable mammalian and viral promoters for the present invention are available in the art. Alternatively, DNA dependent RNA polymerase promoters from bacteria or bacteriophage, e.g. SP6, T7, and T3, may be employed for use in vivo, with the matching RNA polymerase being provided to the cell, either via a separate plasmid, RNA vector, or viral vector. In a specific embodiment, the matching RNA polymerase can be stably transformed into a helper cell line under the control of an inducible promoter. Constructs that function within a cell can function as autonomous plasmids transfected into the cell or they can be stably transformed into the genome. In a stably transformed cell line, the promoter may be an inducible promoter, so that the cell will only produce the RNA polymerase encoded by the stably transformed construct when the cell is exposed to the appropriate stimulus (inducer). The helper constructs are introduced into the stably transformed cell concomitantly with, prior to, or after exposure to the inducer, thereby effecting expression of the alphavirus structural proteins. Alternatively, constructs designed to function within a cell can be introduced into the cell via a viral vector, e.g. adenovirus, poxvirus, adeno-associated virus, SV40, retrovirus, nodavirus, picornavirus, vesicular stomatitis virus, and baculoviruses with mammalian pol II promoters.

Once an RNA transcript (mRNA) encoding the helper or RNA replicon vectors of this invention is present in the helper cell (either via in vitro or in vivo approaches, as described above), it is translated to produce the encoded polypeptides or proteins. The initiation of translation from an mRNA involves a series of tightly regulated events that allow the recruitment of ribosomal subunits to the mRNA. Two distinct mechanisms have evolved in eukaryotic cells to initiate translation. In one of them, the methyl-7-G(5')pppN structure present at the 5' end of the mRNA, known as "cap", is recognized by the initiation factor eIF4F, which is composed of eIF4E, eIF4G and eIF4A. Additionally, pre-initiation complex formation requires, among others, the concerted action of initiation factor eIF2, responsible for binding to the initiator tRNA-$Met_i$, and eIF3, which interacts with the 40S ribosomal subunit (reviewed in Hershey & Merrick. Translational Control of Gene Expression, pp. 33-88. Cold Spring Harbor, N.Y.: Cold Spring Harbor Laboratory Press. 2000.)

In the alternative mechanism, translation initiation occurs internally on the transcript and is mediated by a cis-acting element, known as an internal ribosome entry site (IRES), that recruits the translational machinery to an internal initiation codon in the mRNA with the help of trans-acting factors (reviewed in Jackson. Translational Control of Gene Expression, pp. 127-184. Cold Spring Harbor Laboratory Press. 2000). During many viral infections, as well as in other cellular stress conditions, changes in the phosphorylation state of eIF2, which lower the levels of the ternary complex eIF2-GTP-tRNA-$Met_i$, results in overall inhibition of protein synthesis. Conversely, specific shut-off of cap-dependent initiation depends upon modification of eIF4F functionality (Thompson & Sarnow, Current Opinion in Microbiology 3, 366-370, 2000).

IRES elements bypass cap-dependent translation inhibition; thus the translation directed by an IRES is termed "cap-independent". Hence, IRES-driven translation initiation prevails during many viral infections, for example picornaviral infection (Macejak & Sarnow. Nature 353, 90-94, 1991). Under these circumstances, cap-dependent initiation is inhibited or severely compromised due to the presence of small amounts of functional eIF4F. This is caused by cleavage or loss of solubility of eIF4G (Gradi et al., Proceedings of the National Academy of Sciences, USA 95, 11089-11094, 1998); 4E-BP dephosphorylation (Gingras et al., Proceedings of the National Academy of Sciences, USA 93, 5578-5583. 1996) or poly(A)-binding protein (PABP) cleavage (Joachims et al., Journal of Virology 73, 718-727, 1999).

IRES sequences have been found in numerous transcripts from viruses that infect vertebrate and invertebrate cells as well as in transcripts from vertebrate and invertebrate genes. Examples of IRES elements suitable for use in this invention include: viral IRES elements from Picornaviruses e.g. poliovirus (PV), encephalomyocarditis virus (EMCV), foot-and-mouth disease virus (FMDV), from Flaviviruses e.g. hepatitis C virus (HCV), from Pestiviruses e.g. classical swine fever virus (CSFV), from Retroviruses e.g. murine leukemia virus (MLV), from Lentiviruses e.g. simian immunodeficiency virus (SIV), or cellular mRNA IRES elements such as those from translation initiation factors e.g. eIF4G or DAP5, from Transcription factors e.g. c-Myc (Yang and Sarnow, Nucleic Acids Research 25: 2800-2807 1997) or NF-κB-repressing factor (NRF), from growth factors e.g. vascular endothelial growth factor (VEGF), fibroblast growth factor (FGF-2), platelet-derived growth factor B (PDGF B), from homeotic genes e.g. *Antennapedia*, from survival proteins e.g. X-Linked inhibitor of apoptosis (XIAP) or Apaf-1, or chaperones e.g. the immunoglobulin heavy-chain binding protein BiP (reviewed in Martínez-Salas et al., Journal of General Virology. 82: 973-984, 2001.)

Preferred IRES sequences that can be utilized in these embodiments are derived from: encephalomyocarditis virus (EMCV, accession # NC001479), cricket paralysis virus (accession # AF218039), Drosophila C virus accession # AF014388, *Plautia stali* intestine virus (accession # AB006531), *Rhopalosiphum padi* virus (accession # AF022937), Himetobi P virus (accession # AB017037), acute bee paralysis virus (accession # AF150629), Black queen cell virus (accession # AF183905), Triatoma virus (accession # AF178440), *Acyrthosiphon pisum* virus (accession # AF024514), infectious flacherie virus (accession # AB000906), and Sacbrood virus (accession # AF092924). In addition to the naturally occurring IRES elements listed above, synthetic IRES sequences, designed to mimic the function of naturally occurring IRES sequences, can also be used. In the embodiments in which an IRES is used for translation of the promoter driven constructs, the IRES may be an insect IRES or another non-mammalian IRES that is expressed in the cell line chosen for packaging of the recombinant alphavirus particles, but would not be expressed, or would be only weakly expressed, in the target host. In those embodiments comprising two IRES elements, the two elements may be the same or different.

Rearranged Alphavirus RNA Replicon Vectors

In all systems described to date which employ alphavirus RNA vector replicons to express a heterologous gene of interest, the portion of the alphavirus genome that encodes the alphavirus nonstructural proteins (nsps) is maintained intact, i.e. it appears in the replicon vectors exactly as it appears in the alphavirus. Disclosed herein is a rearranged alphavirus RNA replicon vector in which the sequence encoding nsp4 has been separated from the sequence encoding nsps1-3 and placed under the control of a separate translational control element, such as an IRES. Although it is under separate control and displaced from the other nonstructural coding sequences, the sequence encoding nsp4 is transcribed from the incoming, plus strand of the virus, so that all nonstructural proteins are produced when the replicon is introduced into the helper cell. The cassette directing expression of the heterologous gene of interest is placed between the two nonstructural gene sequences, which together encode all of the alphavirus nonstructural proteins.

In the existing tripartite alphavirus replicon systems (two helper molecules and the vector replicon), recombination between the helper(s) and the replicon is required to generate a replication-competent virus. In these systems, it is generally thought that the viral polymerase complex moves between the helper molecules and the replicon molecule ("strand-switching"), replicating sequences from all three molecules. In these systems, the strand-switching may occur anywhere in the replicon 3' to the 26S promoter directing expression of the heterologous RNA, and still replicate all of the nonstructural polyprotein coding region "nsps1-4". In the rearranged replicons claimed herein, the theoretical frequency of generation of a replication-competent virus is much lower, since any recombination into the heterologous gene region results in the loss of the downstream nsp4 gene in the recombinant.

Thus, described herein is a recombinant nucleic acid comprising, in order: (i) a first nucleic acid sequence encoding a 5' alphavirus replication recognition sequence, (ii) a second nucleic acid encoding alphavirus nonstructural proteins nsp1, nsp 2, and nsp3; (iii) an IRES, (iv) a nucleic acid sequence encoding at least one heterologous gene of interest, (v) an IRES, (vi) a third nucleic acid encoding the alphavirus nonstructural protein nsp4, and (vii) a fourth nucleic acid encoding a 3' alphavirus replication recognition sequence. In another embodiment, element (iii) is a transcriptional promoter, such as the alphavirus subgenomic promoter (also referred to as the 26S promoter or the viral junction region promoter). In certain embodiments, this vector replicon RNA is transcribed in vitro from a DNA plasmid and then introduced into the helper cell by electroporation. In other embodiments, the vector replicon RNA of this invention is transcribed in vivo from a DNA vector plasmid that is transfected into the helper cell (e.g. see U.S. Pat. No. 5,814,482), or it is delivered to the helper cell via a virus or virus-like particle.

The heterologous gene of interest, also referred to herein as a heterologous RNA or heterologous sequence, can be chosen from a wide variety of sequences derived from viruses, prokaryotes or eukaryotes. Examples of categories of heterologous sequences include, but are not limited to, immunogens, cytokines, toxins, therapeutic proteins, enzymes, antisense sequences, and immune response modulators.

In a preferred embodiment, the 3' alphavirus non-coding sequence used in the replicon construct is approximately 300 nucleotides in length, which contains the 3' replication recognition sequence. The minimal 3' replication recognition sequence, conserved among alphaviruses, is a 19 nucleotide sequence (Hill et al., Journal of Virology, 2693-2704, 1997). The 3' non-coding sequence can be modified through standard molecular biological techniques to minimize the size of the 3' end while preserving the replication function.

Resolving DNA Helpers

Several specific embodiments of the resolving DNA helper constructs are disclosed hereinbelow. In one embodiment, this invention discloses a recombinant DNA molecule for expressing alphavirus structural proteins comprising a promoter directing the transcription of RNA from a DNA sequence comprising, in order: (i) a first nucleic acid sequence encoding at least one alphavirus structural protein, (ii) a second nucleic acid sequence encoding a ribozyme, (iii) a third nucleic acid sequence encoding an IRES, and (iv) a fourth nucleic acid sequence encoding at least one alphavirus structural protein, wherein at least one alphavirus structural protein encoded by the fourth nucleic acid sequence is not encoded by the first nucleic acid sequence. In a preferred embodiment, the promoter is a pol II promoter, such as the CMV promoter.

In a further specific embodiment thereof, the first nucleic acid sequence is selected from the group of nucleic acid sequences encoding: capsid, E1 glycoprotein, E2 glycoprotein, E1 and E2 glycoprotein, capsid and E1 glycoprotein, or capsid and E2 glycoprotein. In these specific embodiments, the structural gene nucleic acid sequence(s) encoded by the fourth nucleic acid sequence is selected from this same group. In a preferred embodiment, the combination of sequences encoded by the first and fourth nucleic acid sequences encompass all the structural proteins required to assemble a recombinant alphavirus particle. In a further specific embodiment, one or more of the alphavirus structural proteins may encode one or more attenuating mutations, for example as defined in U.S. Pat. Nos. 5,792,462 and 6,156,558. Specific attenuating mutations for the VEE E1 glycoprotein include an attenuating mutation at any one of E1 amino acid positions 81, 272 or 253. Alphavirus replicon particles made from the VEE-3042 mutant contain an isoleucine substitution at E1-81, and virus replicon particles made from the VEE-3040 mutant contain an attenuating mutation at E1-253. Specific attenuating mutations for the VEE E2 glycoprotein include an attenuating mutation at any one of E2 amino acid positions 76, 120, or 209. Alphavirus replicon particles made from the VEE-3014 mutant contain attenuating mutations at both E1-272 and at E2-209 (see U.S. Pat. No. 5,792,492). A specific attenuating mutation for the VEE E3 glycoprotein includes an attenuating mutation consisting of a deletion of E3 amino acids 56-59.

Virus replicon particles made from the VEE-3526 mutant contain this deletion in E3 (aa56-59) as well as a second attenuating mutation at E1-253. Specific attenuating mutations for the S.A.AR86 E2 glycoprotein include an attenuating mutation at any one of E2 amino acid positions 304, 314, 372, or 376.

In another embodiment, this invention discloses a recombinant DNA molecule for expressing alphavirus structural proteins comprising a promoter directing the transcription of RNA from a DNA sequence comprising, in order: (i) a first nucleic acid sequence encoding a 5' alphavirus replication recognition sequence, (ii) a second nucleic acid sequence encoding either (a) an RNA sequence that promotes transcription of a protein coding RNA sequence or (b) an IRES; (iii) a third nucleic acid sequence encoding at least one alphavirus structural protein, (iv) a fourth nucleic acid sequence encoding a 3' alphavirus replication recognition sequence, (v) a fifth nucleic acid sequence encoding a ribozyme, (vi) a sixth nucleic acid sequence encoding an IRES, and (vii) a seventh nucleic acid sequence encoding at least one alphavirus structural protein, wherein at least one alphavirus structural protein encoded by the seventh nucleic acid sequence is not encoded by the third nucleic acid sequence. In a preferred embodiment, the promoter is a pol II promoter, such as the CMV promoter. In another embodiment, the promoter is the T7 promoter, and the T7 polymerase is provided in the packaging cell in any one of the methods described hereinabove. In a specific embodiment thereof, the third nucleic acid sequence is selected from the group of nucleic acid sequences encoding: capsid, E1 glycoprotein, E2 glycoprotein, E1 and E2 glycoprotein, capsid and E1 glycoprotein, or capsid and E2 glycoprotein. In these specific embodiments, the structural gene nucleic acid sequence(s) encoded by the seventh nucleic acid sequence is selected from this same group. In a preferred embodiment thereof, the combination of sequences encoded by the third and seventh nucleic acid sequences encompass all the structural proteins required to assemble a recombinant alphavirus particle. In a further specific embodiment, the sequences encoded by the third nucleic acid comprise one or more of the alphavirus glycoprotein genes, and the sequence encoded by the seventh nucleic acid comprises the alphavirus capsid gene. In a further specific embodiment, one or more of the alphavirus structural proteins may encode one or more attenuating mutations, as defined in U.S. Pat. Nos. 5,792,462 and 6,156,558, and specific examples of which are listed hereinabove.

In another embodiment, this invention discloses a recombinant DNA molecule for expressing alphavirus structural proteins comprising a promoter directing the transcription of RNA from a DNA sequence comprising, in order: (i) a first nucleic acid sequence encoding an IRES, (ii) a second nucleic acid sequence encoding at least one alphavirus structural protein, (iii) a third nucleic acid sequence encoding a ribozyme, (iv) a fourth nucleic acid sequence encoding an IRES, and (v) a fifth nucleic acid sequence encoding at least one alphavirus structural protein, wherein at least one alphavirus structural protein encoded by the fifth nucleic acid sequence is not encoded by the second nucleic acid sequence. In a preferred embodiment, the promoter is a pol II promoter, such as the CMV promoter. In another embodiment, the promoter is the T7 promoter, and the T7 polymerase is provided in the packaging cell in any one of the methods described hereinabove. In a specific embodiment thereof, the second nucleic acid sequence is selected from the group of nucleic acid sequences encoding: capsid, E1 glycoprotein, E2 glycoprotein, E1 and E2 glycoprotein, capsid and E1 glycoprotein, or capsid and E2 glycoprotein. In these specific embodiments, the structural gene nucleic acid sequence(s) encoded by the fifth nucleic acid sequence is selected from this same group. In a preferred embodiment thereof, the combination of sequences encoded by the second and fifth nucleic acid sequences encompass all the structural proteins required to assemble a recombinant alphavirus particle. In a further specific embodiment, one or more of the alphavirus structural proteins may encode one or more attenuating mutations, as defined in U.S. Pat. Nos. 5,792,462 and 6,156,558, and specific examples of which are listed hereinabove.

As described above, the resolving ability of the DNA helper constructs derives from the insertion of a ribozyme. Ribozymes are catalytic RNA molecules possessing the ability to specifically catalyze its own (cis-) or other (trans-) single-stranded RNA excision (cleavage) following transcription of the RNA in vivo from the DNA vector. Ribozymes target a specific RNA sequence, and different ribozymes target different RNA sequences. Through the insertion of nucleotide sequences encoding these ribozymes into the DNA vector, it is possible to engineer molecules that will recognize specific nucleotide sequences within an RNA transcript and cleave it (Cech, T. Amer. Med. Assn., 260:3030, 1988). When a single DNA helper construct as described herein is introduced into a packaging cell, the ribozyme cleaves the single RNA transcript synthesized in vivo from the introduced DNA construct at the ribozyme target sequence, resulting in the generation of two separate RNA molecules within the cell, each encoding one or more than one alphaviral structural proteins.

A wide variety of ribozymes may be utilized within the context of the present invention, including for example, Group I intron ribozymes (Cech et al., U.S. Pat. No. 4,987,071); Group II Introns (Michel, et al., EMBO J. 2:33-38 1983), hairpin ribozymes (Hampel et al., Nucl. Acids Res. 18:299-304, 1990, U.S. Pat. No. 5,254,678 and European Patent Publication No. 0 360 257), hammerhead ribozymes (Rossi, J. J. et al., Pharmac. Ther. 50:245-254, 1991; Forster and Symons, Cell 48:211-220, 1987; Haseloff and Gerlach, Nature 328:596-600, 1988; Walbot and Bruening, Nature 334:196, 1988; Haseloff and Gerlach, Nature 334:585, 1988), hepatitis delta virus ribozymes (Perrotta and Been, Biochem. 31:16, 1992); *Neurospora* Vakrud satellite (VS) ribozymes (Anderson and Collins, Mol. Cell 5: 4690478, 2000, RNase P ribozymes (Takada et al., Cell 35:849, 1983); as well as other types of ribozymes (see e.g., WO 95/29241, and WO 95/31551). Further examples of ribozymes include those described in U.S. Pat. Nos. 5,116,742, 5,225,337 and 5,246,921.

The Group I intron ribozyme was the first known ribozyme which was described by Cech and colleagues in Tetrahymena in 1982 (Kruger et al. Cell 31: 147-157, 1992). This ribozyme was found to be involved in the processing of ribosomal RNA (rRNA) through a unique self-splicing manner. The self-splicing of rRNA occurs by a two step mechanism. First, a guanine nucleotide is added to the 5' end of the intron as the intron-exon junction is being cleaved. Then the freed 5' intron with guanine attacks at the 3' intron-exon junction to release the intron and generate spliced exons (Zaug et al. Nature 324:429-433 1986). Ribonuclease P contains a catalytic RNA and a small subunit protein. It was discovered in bacteria and is able to generate a mature 5' end of tRNA by endonucleocatalytic cleavage of precursor transcripts (Guerrier-Takada et al. Cell 35: 849-857 1983). The mechanism of cleavage by a hammerhead ribozyme has been characterized in the art [see, e.g., Reddy et al., U.S. Pat. No. 5,246,921; Taira et al., U.S. Pat. No. 5,500,357; Goldberg et al., U.S. Pat. No. 5,225,347].

While an understanding of the precise mechanism of the ribozyme is not necessary to practice the claimed invention, it is generally thought that the ribozyme is attached to the substrate RNA molecule by forming two paired regions via Watson-Crick pairing between the RNA substrate sequence and the two binding regions of the ribozyme. The first deprotonation reaction takes place in the 2' sugar at the 3' side of the substrate cleavage site. This deprotonation causes nucleophilic attack of the adjacent phosphodiester bond and subsequently protonation of the 5' oxyanion cleaving group thereby generating, 2',3'-cyclic phosphate and a 5' hydroxyl terminus.

Like the hammerhead ribozyme, the hairpin ribozyme was also found in plant viroids, and it acts by a similar mode of action to the hammerhead ribozyme (Feldstein et al. Gene 82:53-61 1989). The design and use of hairpin ribozymes for cleaving an RNA substrate has been described in the art (Hampel et al., U.S. Pat. No. 5,527,895).

Generally, the targeted sequence of a ribozyme can vary from approximately 3 to 20 nucleotides long. The length of this sequence is sufficient to allow a hybridization with target RNA and disassociation of the ribozyme from the cleaved RNA.

Haseloff et al (U.S. Pat. No. 6,071,730) describe trans-splicing ribozymes that also provide precise cleavage sites. Trans-splicing ribozymes may be used in alternative embodiments to those described above, in which the element of the recombinant nucleic acid that comprises a ribozyme is substituted therefor with a ribozyme target sequence. The ribozyme itself is then provided in trans as a separate DNA or RNA molecule.

Thompson et al. (U.S. Pat. No. 6,183,959) describe at least seven basic varieties of enzymatic RNA molecules which are derived from naturally occurring self-cleaving RNAs. In the embodiments of the invention which employ a ribozyme, an alternative embodiment employs the use of a pol III promoter, since ribozymes often have extensive secondary structure that may be more efficiently transcribed by such a promoter.

As described hereinabove, in one set of embodiments of this invention, one or more of the nucleic acid sequences encoding the alphavirus structural proteins is/are placed between the 5' and 3' alphavirus replication recognition sequences, resulting in amplification of this nucleic acid by the alphavirus replicase proteins. In preferred embodiments, a minimal 5' alphavirus replication recognition sequence is utilized. In a specific embodiment, all of the alphavirus structural proteins are expressed from a single promoter. The single transcript is then resolved through a precise cleavage at the ribozyme site into two replicable (i.e. amplifiable) RNAs (replicable due to the presence of the 5' and 3' alphavirus replication recognition sequences), each encoding only a subset of the alphavirus structural proteins. These RNAs are then translated from IRES sequences located 5' to the structural protein coding sequences.

In a specific, preferred embodiment of the invention, the Hepatitis Delta virus (HDV) ribozyme is utilized (Wu et al. Science 243:652-655, 1989). The RNA of the hepatitis delta virus has autocatalytic RNA processing activity similar to that of hammerhead and hairpin ribozymes, and the ribozyme cleavage points of both delta strands and the domains containing them are clearly defined. The HDV ribozyme is approximately 80-90 nucleotides in length and only functional in cis. Advantages in using this ribozyme are (i) there are no specific sequence requirements at the 5' cleavage site and (ii) the cleavage product is generated with defined 3' ends. As described in U.S. Pat. No. 5,225,337 (incorporated herein by reference), a preferred embodiment for an HDV ribozyme is a sequence consisting of at least 18 consecutive nucleotides from the conserved region of HDV, in which the conserved region of the HDV RNA is found within either the region of HDV having ribozyme activity between residues 611 and 771 on the genomic strand or the region between residues 845 and 980 on the complementary anti-genomic strand. The selected sequence having ribozyme activity cleaves the target RNA molecule to form a 2',3' cyclic phosphate and 5' hydroxyl.

In certain embodiments of this invention, additional sequence alterations are made downstream from the ribozyme region. The ribozyme cleavage event results in a clean 3' end, such that the nucleotide sequence remains unchanged. With some ribozymes, the 5' end of the downstream molecule resulting from the cleavage event may contain residual ribozyme sequence, and the potential secondary structure of this residual sequence may have detrimental effects on downstream translational activity, e.g. driven by an IRES, or upon any other functional role of the 5' sequence of the downstream fragment. Thus, to minimize the potential for such interference, in some embodiments of this invention it may be useful to include a region of non-translated irrelevant nucleotide sequence downstream from the ribozyme sequence. In an alternative embodiment to generate a clean 5' end, a second antigenomic ribozyme, e.g. HDV, can be added downstream from the sense ribozyme. This second ribozyme would be functional only on the negative sense strand, and thus it would generate its clean "3' end" on the 5' end of the downstream sequence.

Resolving RNA Helpers

In another embodiment of resolving helpers of this invention, the helper construct is a DNA helper in which the promoter is a DNA-dependent RNA polymerase promoter, such as the T7 polymerase promoter, and this promoter directs more than one alphavirus structural protein; preferably capsid and at least one glycoprotein. The helper further encodes a protease recognition sequence which is inserted in-frame between coding sequences for the alphavirus structural proteins. Thus, disclosed is a recombinant DNA molecule for expressing alphavirus structural proteins comprising: (i) a DNA dependent RNA polymerase promoter, (ii) an IRES (iii) a nucleic acid sequence encoding at least one alphavirus structural protein, (iv) a non-autocatalytic protease recognition site, and (v) a nucleic acid sequence encoding at least one alphavirus structural protein, wherein the nucleic acid sequences in (iii) and (v) are not identical.

In a separate embodiment, a DNA helper for expressing a resolving RNA helper in vivo is provided comprising (i) a DNA dependent RNA polymerase promoter, (ii) a nucleic acid sequence encoding at least one alphavirus structural protein, (iii) a non-autocatalytic protease recognition site, and (iv) a nucleic acid sequence encoding at least one alphavirus structural protein, wherein the nucleic acid sequences in (ii) and (iv) are not identical. In a preferred embodiment, the promoter is an RNA polymerase II promoter, such as the CMV promoter.

In another embodiment, the RNA helper is produced in vitro from a recombinant DNA molecule comprising a promoter directing the transcription of RNA from a DNA sequence comprising (i) a first nucleic acid sequence encoding an alphavirus 5' replication recognition sequence, (ii) a transcriptional promoter, (iii) a nucleic acid sequence encoding at least one alphavirus structural protein, (iv) a non-autocatalytic protease recognition site, and (v) a nucleic acid sequence encoding at least one alphavirus structural protein, and (vi) an alphavirus 3' replication recognition sequence, wherein the nucleic acid sequences of (iii) and (v) are not identical. In preferred embodiments, the promoter is the T7 promoter and the transcription promoter of element (ii) is an alphavirus subgenomic promoter.

In preferred embodiments of these helpers, the construct produces the polyprotein Capsid-protease site-E2-E1. In other embodiments, the polyprotein is E2-E1-protease site-Capsid or Capsid-E1-protease site-E2. Signal sequences, such as E3 or 6k, are included as appropriate, with E1 and/or E2 sequences. In those constructs which encode an alphavirus capsid protein, the capsid protein should be modified to remove the active site for the autoproteolytic activity of capsid (see U.S. Pat. No. 5,792,462; Col 11, lines 9-19; Strauss et al. 1990 Seminars in Virology 1:347).

The protease recognition sequence is preferably a relatively rare sequence that does not occur frequently in the coding sequences of the helper cell. Examples of such proteases are widely known in the art such as factor Xa, enteropeptidase and thrombin, but some of these proteases have exhibited lowered specificity for their target recognition/ cleavage sites and have cleaved proteins at non-canonical sites. For this reason, the use of a rare protease with a specific cleavage recognition site which would be unlikely to be present in the host cell or aiphaviral protein repertoire would be a preferred embodiment in this invention. An example of such a rare protease site is that of the tobacco etch virus Ma protease (TEV protease). TEV protease cleaves the amino acid sequence ENLYFQG (SEQ ID NO:50) between Q and G with high specificity. In addition, recent advances in the art have demonstrated the activity of TEV protease can be increased significantly by a number of methods. One method includes increasing the solubility of the protease by producing it in the form of a fusion protein. The second ablates the inherent auto-catalytic function of the protease which severely reduces the functional levels of protease within the cell. Using standard mutagenesis techniques the autocatalytic domain has been altered and leads to maintenance of high levels of the protease in its active form (Kapust et al., Protein Engineering, 14:993-1000, 2001). In the rare event that the consensus cleavage recognition site is present within the alphaviral vector or the host cell, alternate proteases may be used in this invention. These alternates would most likely be derived from non-mammalian origins to lessen the chance that the protease would recognize mammalian sequences. Such proteases would preferably include proteases derived from members of the Potyvirus family of plant viruses such as Turnip mosaic potyvirus (TuMV) which recognizes an amino acid sequence XVRHQ (SEQ ID NO:51) where X is any aliphatic amino acid. The invention can also utilize other proteases such as Wheat streak mosaic virus, plum pox virus, potato virus Y, tobacco vein mottling virus, *Ornithogalum* mosaic virus, yam mosaic virus, shallot potyvirus, bean yellow mosaic virus, papaya ringspot virus, pea seed-borne mosaic virus, Johnson grass mosaic virus, rye grass mosaic virus, sweet potato mild mottle virus, or any other members of the family of C4 unassigned peptidases. The only required feature of the protease in this invention is its restricted ability to recognize only the target sequence in the vector construct and to lack non-specific protease activity that could cleave host or other aiphaviral sequences.

In the foregoing embodiments comprising a protease recognition site, the promoter directs the expression of all encoded alphavirus structural proteins. The DNA helpers are introduced into the helper cell along with a source of T7 polymerase (e.g. a stably transformed expression cassette, a separate expression plasmid, or the polymerase protein), a single RNA transcript is produced from the promoter which contains the IRES to direct cap-independent translation of a polyprotein, which is then cleaved by the protease provided in the helper cell. The RNA helper, transcribed from a DNA helper vector in vitro, is introduced to the helper cell, preferably by electroporation, where it is amplified and translated into the polyprotein. As above, the protease is provided to the helper cell in any one of several formats, and the polyprotein is cleaved in the presence of the protease.

In a specific embodiment, the protease may be present as a stably transformed cassette in the genome of the helper cell. In this embodiment, the gene encoding the protease is preferably under the control of an inducible promoter, such a heat shock or metallothionen-responsive promoter. In another embodiment, the protease gene and/or the T7 polymerase gene can be present in the helper cell as an alphavirus subgenomic expression cassette, comprising an alphavirus 5'end, an alphavirus subgenomic promoter directing expression of the protease, and an alphavirus 3' end. This cassette is inducible in the helper cell, being expressed only upon introduction of the alphavirus RNA replicon to the cell. Alternatively, the protease may be added to the helper cell concomitantly with the RNA helper and the RNA replicon, either as a separately translatable RNA or as protein.

Non-replicating DNA Helper

In another set of embodiments of this invention, a DNA helper that does not incorporate the alphavirus replication recognition sequences that allow amplification of the RNA encoded between the sequences is disclosed. Lacking such sequences, which can contribute to the frequency of functional recombinant molecules that may be generated in the helper cell, a single DNA helper encoding all the alphavirus structural proteins necessary to produce recombinant alphavirus particles can minimize the effect that packaging/ recombination may have in a helper cell. The decrease in packaging/recombination detected, as compared to the bipartite RNA system, is at least one order of magnitude lower; in preferred embodiments, it is two, three, or four orders of magnitude lower. Thus, another embodiment of the claimed invention comprises a recombinant DNA for expressing alphavirus structural proteins comprising a promoter operably linked to a nucleotide sequence encoding all the alphavirus structural proteins. In a preferred embodiment, the promoter is an RNA polymerase II promoter, such as the CMV promoter.

Preferred methods for introducing this DNA helper to alphavirus-permissive cells are also disclosed, including the use of cationic lipids, such as FuGene® and Lipofectamine®, electroporation, or viral vectors. The combination of cell type and transfection method can be optimized by testing of such combinations according to the methods disclosed herein. In specific embodiments, 293T and Vero cells can be used. In a preferred embodiment, the DNA helper is introduced prior to the introduction of the replicon RNA, e.g. thirty minutes, 1, 2, 3, 4, 5, 6, 7, 8, 9, 10, 12, 24, or 48 hours prior to electroporation of the replicon RNA into the cells. Any amount of time that results in no significant decrease in the transfection efficiency of the replicon RNA and allows sufficient packaging of VRPs by the cells is suitable.

In an alternative embodiment, the DNA helpers of this invention may be co-electroporated into the helper cells with an alphavirus replicon RNA. The parameters of electroporation are adjusted from those used for solely RNA or DNA electroporation to optimize the yield of VRPs from the helper cells.

Chimeric Alphavirus RNA Helpers

In another set of embodiments, an RNA helper which utilizes replication recognition signals (5' and 3') from alphaviruses other than the alphavirus from which the structural proteins are derived is disclosed. In these embodiments, the promoter directs the expression of at least one structural protein and the alphavirus 5' and 3' ends that direct replication of the helper allow amplification, but the frequency of packaging/recombination by these helpers is reduced, due to the inefficient or complete lack of recognition of packaging signals of the one alphavirus by the alphavirus structural proteins of the other alphavirus. In a preferred embodiment, the RNA helper of this invention encodes one or more VEE structural proteins and utilizes the replication recognition signals from an alphavirus selected from the group consisting of Sindbis (particularly TR339), S.A.AR86, Semliki Forest Virus, or Ross River Virus.

Non-alphavirus RNA Helpers

In another set of embodiments of this invention, helper constructs that express one or more alphavirus structural proteins are disclosed which utilize viral RNA replication machinery derived from a virus other than an alphavirus. Disclosed is an alphavirus structural protein expression system, comprising two RNA molecules, wherein (a) a first RNA encodes sequences for viral replicase proteins, and (b) a second recombinant RNA encodes sequences for (i) the 5' replication recognition sequence for a replication complex comprising the viral replicase proteins of (a), (ii) one or more alphavirus structural proteins, and (iii) the 3' replication recognition sequence for the replication complex comrising the viral replicase proteins of (a). Following introduction of the two RNA molecules into the helper cell, the first RNA replicates the second RNA encoding one or more alphavirus structural proteins, and then the helper cell's translational machinery translates the structural protein sequence(s) encoded on the second recombinant RNA.

In a preferred embodiment, the first and second RNA molecules are derived from a nodavirus. The *Nodaviridae* are a family of small, non-enveloped, isometric viruses with bipartite positive-sense RNA genomes (Ball & Johnson, 1998 In *The Insect Viruses*, pp. 225-267. Edited by L. K. Miller & L. A. Ball. New York:Plenum). The nodavirus genomes are among the smallest of all known animal viruses, containing less than 5 kb of genetic material. Genomic nodavirus RNA is infectious to insect, plant (Selling, B. H., et al., Proc. Natl. Acad. Sci. USA 87:434-438, 1990) and mammalian (Ball, L. A., et al., J. Virol. 66:2326-2334, 1992) cells. Nodaviruses use unique regulatory cis-elements, including nodaviral-specific RNA replication (Zhong, W., et al., Proc. Natl. Acad. Sci. USA 89:11146-11150, 1992; Ball, L. A. and Li, Y., J. Virol. 67:3544-3551, 1993; Li, Y. and Ball, L. A., J. Virol. 67:3854-3860, 1993; Ball, L. A., J. Virol. 69:720-727, 1995) and packaging signals (Zhong, W., et al., supra, 1992). Both genome segments are capped at their 5' ends but lack poly(A) tails (Newman & Brown, 1976. *Journal of General Virology* 30, 137-140). The smaller segment, referred to as RNA2, encodes a precursor to the nodavirus coat, or capsid, protein. The larger segment, referred to as RNA1, encodes the viral portion of the RNA-dependent RNA polymerase (RdRp), which replicates both RNA1 and 2 (Ball & Johnson, 1998, ibid.). The RNA1 of nodaviruses are notable for their ability to synthesize high cytoplasmic levels of capped and functional mRNAs, i.e. RNA1 and RNA2. The sequences of several nodavirus RNA1 molecules have been reported recently, and the RNA2 sequences have been previously disclosed (see Johnson et al. 2001 J. Gen. Virol. 82:1855-1866 and references cited therein, including GenBank accession numbers).

Applicants have determined that nodavirus replication and alphavirus replication can occur at the same time within the same cell. Thus, in one set of embodiments of this invention, a nodavirus-based alphavirus structural protein expression system is disclosed, in which RNA1 of a selected nodavirus is supplied to a cell in which recombinant alphavirus particles are to be packaged, along with an engineered RNA2 from the same or a different nodavirus. The RNA2 is engineered to remove part of the coding sequence for the nodavirus capsid gene and substitute therefor the coding sequence for at least one alphavirus structural protein. In a specific embodiment of the methods of this invention, these two nodavirus RNAs (i.e. RNA1 and engineered RNA2) are co-electroporated with an alphavirus RNA replicon into a cell in which all three RNAs are expressed. In a preferred embodiment, a nodavirus RNA1, a recombinant nodavirus RNA2 expressing an alphavirus capsid gene, an alphavirus RNA replicon, and a second helper RNA expressing alphavirus glycoproteins are co-electroporated into a cell in which all four RNAs can be expressed, resulting in the packaging of the replicon into recombinant alphavirus particles. Suitable nodaviruses for use in the claimed invention include Nodamura virus (NoV), Flock House virus (FHV), Black Beetle virus (BBV), Boolarra virus (BoV), Gypsy moth virus (GMV), and Manawatu virus (MwV). Preferred nodaviruses are FHV and NoV. In another embodiment, the RNA1 and recombinant RNA2 are introduced into the helper cell by a virus or a virus-like particle, such as adenovirus, vaccinia, poxvirus, SV-40, adeno-associated Virus, retrovirus, nodavirus, picornavirus, vesicular stomatitis virus, and baculoviruses with mammalian pol II promoters.

Methods for Making Alphavirus Replicon Particles

Methods for making alphavirus replicon particles expressing one or more heterologous sequences which utilize the helpers and/or the alphavirus RNA replicons of this invention are also disclosed. Using the methods of this invention, preparations of alphavirus replicon particles are produced which contain no detectable replication-competent alphavirus particles, as determined by passage on alphavirus-permissive cells in culture.

To make the particles, a helper or combination of helpers is selected such that it provides all alphavirus structural proteins necessary to assemble an infectious particle. In preferred embodiments, the helper or combination of helpers encode capsid, E1 and E2. In an embodiment comprising more than one helper, one of the helpers may be selected from the helpers known in the art, e.g. the standard split RNA helpers referenced herein. A helper or combination of helpers comprising at least one embodiment of this invention can be used to package any alphavirus replicon RNA. In preferred embodiments, the alphavirus replicon RNA is a rearranged alphavirus RNA replicon as claimed herein or the standard alphavirus replicon RNA referenced herein. In specific, preferred embodiments, the alphavirus replicon particles are VEE-based particles, i.e. the helpers encode VEE alphavirus structural proteins and the replicon RNA is derived from VEE.

Alphavirus replicon particles are prepared according the methods disclosed herein in combination with techniques known to those skilled in the art. The methods include first introducing the selected helper(s) and an alphavirus replicon RNA encoding one or more heterologous RNAs into a population of alphavirus-permissive cells, and then incubating the cells under conditions that allow for the production of alphavirus replicon particles. The step of introducing the helper(s) and alphavirus replicon RNA to the population of helper cells can be performed by any suitable means, as disclosed herein or known to those generally skilled in the art. As described herein, the population of cells may be a stably transformed cell line that provides a promoter, a trans-acting ribozyme, a protease, or any combination thereof. Alternatively, said promoters, trans-acting ribozymes or proteases may be added to the population of cells in the form of separately relicable or non-replicable nucleic acids or proteins, as applicable.

Compositions or preparations of alphavirus replicon particles are collected from the population of helper cells using conventional techniques know to those skilled in the art, e.g. U.S. Pat. Nos. 5,492,462; 6,156,558; and these compositions are characterized by the fact that they will contain no detectable, replication-competent alphavirus particles, as measured by passage on alphavirus-permissive cells in culture.

As will be understood by one skilled in the art, there are several embodiments and elements for each aspect of the claimed invention, and all combinations of different elements are hereby anticipated, so the specific combinations exemplified herein are not to be construed as limitations in the scope of the invention as claimed. If specific elements are removed or added to the group of elements available in a combination, then the group of elements is to be construed as having incorporated such a change.

All references cited herein, including publications, patent applications, and patents, are hereby incorporated by reference to the same extent if each was individually and specifically indicated to be incorporated by reference, and was reproduced in its entirety herein.

TABLE 1

PCR primers for Resolving DNA helper cloning

| Primer name | Sequence | Amplification product |
|---|---|---|
| GP forward | 5'CTAGCTAGCTATGTCACTAGTGACCACCATG3' (SEQ ID NO: 1) | VEE glycoprotein |
| GP reverse | 5' GGGCCCTCAATTATGTTTCTGGTTGGT 3' (SEQ ID NO: 2) | VEE glycoprotein |
| GP-2 forward | 5' GCAGAGCTGGTTTAGTGAACCGTATAGGCGGCGCATGAGA GAAGCCCAGACCA 3' (SEQ ID NO: 3) | VEE glycoprotein |
| GP-2 reverse | 5' GCTAGCGCTCTTCCCTTTTTTTTTTT 3' (SEQ ID NO: 4) | VEE glycoprotein |
| Capsid forward | 5' GCTCTAGAATGTTCCCGTTCCAGCCAATG 3' (SEQ ID NO: 5) | VEE capsid |
| Capsid reverse | 5'GCGTCGACGTCTTGGCCATAGCGGCCGCGGTTACAGACAC ATGGTGGTCACT 3' (SEQ ID NO: 6) | VEE capsid |
| hdR Forward | 5'CGGGTCGGCATGGCATCTCCACCTCCTCGCGGTCCGACCT GGGCATCCGAAGGAGGACGTCGTCCACTCGGATGGCTAAG GGAGAGCTCGC 3' SEQ ID NO: 7) | Hepatitis delta ribozyme |
| hdR Reverse | 5'TCGAGCGAGCTCTCCCTTAGCCATCCGAGTGGACGACGTC CTCCTTCGGATGCCCAGGTCGGACCGCGAGGAGGTGGAGAT GCCATGCCGACCCGGGCC 3' (SEQ ID NO: 8) | Hepatitis delta ribozyme |
| CMV forward | 5' TAGTTATTAATAGTAATCAATTACGG 3' (SEQ ID NO: 9) | CMV IE promoter |
| CMV reverse | 5'TGGTCTGGGCTTCTCTCATGCGCCGCCTATACGGTTCACTA AACCAGCTCTGC 3' (SEQ ID NO: 10) | CMV IE promoter |
| d26S forward | 5' GGCGCGCCGTCCTCCGATCGTTGTCAGAAG 3' (SEQ ID NO: 11) | CMV IE + VEE 5' NCR |
| d26S reverse | 5' GGCGCGCCTCCGTCAACCGCGTATACATCCTGGTAA 3' (SEQ ID NO: 12) | CMV IE + VEE 5' NCR |
| E3 forward | 5' GGCGCGCCATGTCACTAGTGACCACCATGTG 3' (SEQ ID NO: 13) | E3-E2-6K genes |
| 6K reverse | 5' CTCGTAGGCGCCGGCGCCTGCGG 3' (SEQ ID NO: 14) | E3-E2-6K genes |
| EMCV forward | 5' GGCGCGCCAATTCCGCCCCTCTCCCTCCC 3' (SEQ ID NO: 15) | EMCV IRES |
| EMCV reverse | 5' GGCGCGCCTTATCATCGTGTTTTTCAAAG 3' (SEQ ID NO: 16) | EMCV IRES |

TABLE 1-continued

PCR primers for Resolving DNA helper cloning

| Primer name | Sequence | Amplification product |
|---|---|---|
| EMCV-2 forward | 5' GCTAGCAATTCCGCCCCTCTCCCTCCC 3 (SEQ ID NO: 17) | EMCV IRES |
| EMCV-2 reverse | 5' GCTAGCTTATCATCGTGTTTTTCAAAG 3' (SEQ ID NO: 18) | EMCV IRES |

TABLE 2

PCR primers for Nodavirus RNA helper cloning

| Primer name | Primer sequence | Amplification product |
|---|---|---|
| Capsid F (MluI) | 5' CGACGCGTATGTTCCCGTTCCAGCCAATG 3' (SEQ ID NO: 19) | VEE capsid MluI |
| Capsid R (MluI) | 5' GCACGCGTTTACAGACACATGGTGGTCACT 3' (SEQ ID NO: 20) | VEE capsid MluI, VEE capsid 1, VEE capsid 2 |
| Capsid F1 (NcoI) | 5' CCTGCCATGGTATAAATGTTCCCGTTCCAACCA ATG 3' (SEQ ID NO: 21) | VEE capsid 1 |
| Capsid F2 (NcoI) | 5' CCTGCCATGGCCCCGTTCCAACCAATG 3' (SEQ ID NO: 22) | VEB capsid 2 |

EXAMPLES

The following examples are provided to illustrate the present invention, and should not be construed as limiting thereof. In these examples, nm means nanometer, mL means milliliter, pfu/mL means plaque forming units/milliliter, nt means nucleotide(s), PBS means phosphate-buffered saline, VEE means Venezuelan Equine Encephalitis virus, EMC means Encephalomyocarditis virus, BHK means baby hamster kidney cells, GFP means green fluorescent protein, Gp means glycoprotein, CAT means chloramphenicol acetyl transferase, IFA means immunofluorescence assay, and IRES means internal ribosome entry site. The expression "E2 amino acid (e.g., lys, thr, etc.) number" indicates the designated amino acid at the designated residue of the E2 gene, and is also used to refer to amino acids at specific residues in the E1 protein and in the E3 protein.

In the Examples that follow, the starting materials for constructing the various helper plasmids can be selected from any of the following: full-length cDNA clones of VEE, i.e. pV3000, the virulent Trinidad donkey strain of VEE; or any of these clones with attenuating mutations: pV3014 (E2 lys 209, E1 thr 272), p3042 (E1 ile 81), pV3519 (E2 lys 76, E2 lys 209, E1 thr 272) and pV3526 (deletion of E3 56-59, E1 ser 253), which are in the genetic background of Trinidad donkey strain VEE. As described in U.S. Pat. No. 5,792,462, these plasmids are digested with restriction enzymes and religated to remove the nonstructural protein coding region. Alternatively, one may start with existing helper plasmids, such as those described in Pushko et al. 1997, Ibid., or as described herein.

Example 1

VEE Replicon Particles

Replicon particles for use as a vaccine or for gene therapy can be produced using the VEE-based vector system (see for example U.S. Pat. No. 5,792,462). In these Examples, one or more attenuating mutations (e.g. Johnston and Smith, Virology 162(2): 437-443 (1988); Davis et al., Virology 171(1): 189-204 (1989); Davis et al., 1990) may have been inserted into VEE sequence to generate attenuated VEE replicon particles (Davis et al., Virology 183(1): 20-31 (1991); Davis et al., Virology 212(1): 102-110 (1995); Grieder et al., Virology 206(2): 994-1006 (1995).

The examples herein describe the construction of an RNA replicon, i.e. an RNA that self-amplifies and expresses, and one or more helper nucleic acids encoding the structural proteins to allow packaging. The replicon RNA carries one or more foreign genes, e.g. a gene encoding an immunogen or a reporter gene. The replicon RNA and the helper nucleic acids (which express the alphavirus structural proteins, as described hereinbelow) are then introduced into a single cell, i.e. the helper or packaging cell, in which the replicon RNA is packaged into virus-like particles (herein referred to as "virus replicon particles" or "VRPs") that are infectious for only one cycle. During the single, infectious cycle, the characteristics of the alphavirus-based vector result in very high levels of expression of the replicon RNA in cells to which the VRP is targeted, e.g. cells of the lymph node.

The resulting vaccine vectors are avirulent and provide complete protection against lethal virus challenge in animals, including but not limited to rodents, horses, nonhuman primates, and humans.

Example 2

Standard VEE Replicons and RNA Helpers

As described in U.S. Pat. No. 5,792,462, Pushko et al., 1997 (Virology 239:389-401), and WO 02/03917 (Olmsted, et al.), a standard alphavirus replicon based on VEE contains the VEE nonstructural genes and a single copy of the 26S subgenomic RNA promoter followed by a multiple cloning site. In a vaccine construct, one or more genes encoding an immunogen are inserted into this cloning site. For purposes of demonstrating the capability of the novel structural protein expression cassettes of this invention, VEE replicons are constructed by inserting the GFP or CAT gene into this cloning site. Expression of these reporter genes from particles made with various combinations of the structural protein expression cassettes described herein demonstrate the utility and novelty of these cassettes.

The standard VEE split RNA helper systems, as described in U.S. Pat. Nos. 5,792,462, Pushko et al., 1997 (*Virology* 239:389-401), and PCT publication WO 02/03917 (Olmsted, et al.), are described herein as "Cap or Gp RNA", "wild-type Gp RNA helper", "glycoprotein helper", "Gp helper RNA", "GP-helper", "capsid helper", or "C-helper". These RNA helpers are made from DNA plasmids as described in the cited references, and these DNA plasmids can be a convenient source for obtaining the structural protein coding fragments, e.g. by PCR amplification. Alternatively, these coding fragments can be obtained from full-length clones of VEE or attenuated variants thereof (see U.S. Pat. No. 5,185,440; U.S. Pat. No. 5,505,947). These standard VEE helpers are used in combination with the helper inventions disclosed herein and/ or in comparative studies with the new systems, as disclosed herein.

Example 3

Rearranged Alphavirus RNA Replicon Vector

The nsP4 region was deleted from a standard VEE GFP-expressing replicon vector (see Example 2) by digestion with AvrII and ApaI restriction enzymes, followed by treatment of the digested DNA with T4 DNA polymerase to generate blunt ends, and re-ligation of the DNA to generate pGFPΔnsP4-1. When RNA transcribed in vitro from the pGFPΔnsP4-1 DNA plasmid is electroporated into cells, GFP is not expressed. However, GFP protein can readily be detected in cells co-electroporated with GFPΔnsP4-1 RNA and an unmodified replicon vector RNA. This demonstrates that the pGFP-ΔnsP4-1 vector can be complemented by nsP4 protein provided in trans by another replicon RNA. This result indicates that the nsp4 gene can function when expressed separately from the other non-structural proteins.

The nsP4 gene (including a portion of nsP3 to maintain an nsP2 protease cleavage site) was then cloned downstream of an EMCV IRES. The nsP4 region was PCR amplified from the standard VEE replicon vector with primers nsP34-forward (SEQ ID NO: 33) and nsP4-stop (SEQ ID NO: 34) (also, see Table 3). The amplified nsP4 gene fragment was cloned into a transfer vector containing an EMCV IRES, using BamHI and XbaI as the 5' and 3' restriction enzyme sites. A second set of primers was then used to amplify the EMCV-nsP4 construct from the transfer vector: EMCV forward-AscI (SEQ ID NO: 35) and EMCV reverse-AscI (SEQ ID NO: 36), also, see Table 3). The EMCV-nsP4 PCR product was digested with AscI restriction enzyme and ligated into AscI linearized pGFPΔnsP4-1 vector DNA, to generate pGFP-ΔnsP4-1.1. The cloned nsP4 gene region (including a portion of nsP3 that contains the nsP2 protease site) was sequenced to ensure that no mutations to the nsP4 gene were introduced during cloning.

RNA transcribed in vitro from pGFPΔnsP4-1.1 DNA was electroporated into Vero, BHK, 293T and CEF cells, and GFP protein expression was detected in all cell types.

TABLE 3

| PCR primers for Rearranged Replicon Vector. | | |
|---|---|---|
| Primer name | Sequence 5'-3' | Region amplified |
| nsP34 forward | CGGGATCCATGCGGTTTGATGCGGGTGCATA CATC (SEQ ID NO: 33) | VEE nsP4 gene |
| nsP4 stop | GCTCTAGATTAGCCGTAGAGAGTTATAGGGG (SEQ ID NO: 34) | VEE nsP4 gene |
| EMCV forward-AscI | TGGCGCGCCGCTCGGAATTCCCCCTCTCCC (SEQ ID NO: 35) | EMCV-nsP4 |
| EMCV reverse-AscI | AGGCGCGCCTTCTATGTAAGCAGCTTGCC (SEQ ID NO: 36) | EMCV-nsP4 |

Example 4

Construction of Helpers with Minimal 5' Alphavirus Replication Recognition Sequence A. Constructs for Determining the Minimal 5' Untranslated Region (UTR)

When VEE replicon particles (VRP) are inoculated onto fresh cultures of Vero cells, at high multiplicities of infection (MOI), capsid protein can be detected by anti-capsid immunofluoresence assay (IFA; see Table 5 below). Detection of capsid protein in VRP infected cells indicates that the capsid gene is present in the VRP. Similar findings to these have been reported by others (Lu and Silver, 2001, ibid.). This may occur in at least three ways: 1) as the result of a recombination event between the capsid helper RNA and a replicon RNA, 2) as the result of copackaging of the capsid helper RNA into a VEE replicon RNA containing particle, or 3) as a result of packaging the capsid helper RNA alone into particles (no VEE replicon RNA present). VEE helpers previously described in the art (Johnston et al., ibid., Pushko et al., ibid.) contain 519 nucleotides of the 5' region of VEE RNA. Specifically, this 5' region encodes a 45 nt untranslated region (UTR) as well as 474 nt of the nsP1 open reading frame (ORF). These helper RNAs were originally designed to remove the VEE nucleotide region thought to be involved in packaging of viral RNAs into particles. This design was based on work carried out using Sindbis virus, in which a region of nsP1, located approximately 1000 nt into the genome, was thought to encode the packaging signal (Bredenbeek, P J et al., 1993 J Virol 67: 6439-6446; Levis et al 1986 Cell 44:137-145; Weiss et at. 1989 J Virol 63:5310-8). To further optimize the helper constructs, increasing deletions were made into the 5' UTR to determine the minimal sequences required for the helpers to provide (i) acceptable VRP yields and (ii) the lowest theoretical frequency for capsid gene copackaging/recombination in VRP preparations.

1. Construction of 5' Truncated VEE Capsid Helpers

A capsid helper plasmid containing the sequence for the VEE capsid gene was constructed as previously described. This construct contains a sequence of 519 nucleotides, the "5' UTR", located upstream (i.e. 5') from the ATG initiation codon for the capsid coding sequence, and is herein referred to as "hcap10".

(a) PCR-based Construction

Nine consecutive deletions of approximately 50 nt each were made in the 519 nt UTR present in the VEE capsid helper (see Example 2). The following deletions were made from the 3' end of the 5' UTR:

| Hcap Construct name: | 5' UTR nt included: |
|---|---|
| 10 | 1-520 |
| 1 | 1-484 |
| 2 | 1-435 |
| 3 | 1-397 |
| 4 | 1-336 |
| 5 | 1-294 |
| 6 | 1-231 |
| 7 | 1-185 |
| 8 | 1-125 |
| 9 | 1-46 |

This initial set of capsid helper ("Hcap") constructs was produced using a PCR method that did not require cloning of individual constructs. The procedure was carried out in two separate steps. First, nine reverse primers (Hcap 1-9 reverse) were designed ~50 nt apart, complementary to the 5' UTR up to position 470 of the VEE replicon, and engineered to contain an ApaI restriction site:

| Primer name | SEQ ID NO: |
|---|---|
| 48-132.pr2 | 39 |
| 48-132.pr4 | 40 |
| 48-132.pr6 | 41 |
| 48-132.pr8 | 42 |
| 48-132.pr10 | 43 |
| 48-132.pr12 | 44 |
| 48-132.pr14 | 45 |
| 48-132.pr16 | 46 |
| 48-132.pr18 | 47 |

The sequences of each of these primers is presented in Table 4. An Hcap forward primer, 13-101.pr1 (SEQ ID NO: 37) (also, see Table 4) was designed so that when it was used in combination with any one of the reverse primers, it would amplify a fragment containing the T7 promoter and the respective 5'UTR deletion. Second, primers were designed to amplify the capsid gene out of the existing capsid helper plasmid such that the fragment would have the following composition: 5' ApaI restriction site, 26S promoter, capsid gene, 3' UTR-3'. These primers are 48-132.pr1 (SEQ ID NO: 48) and 3-8pr4 (SEQ ID NO: 49) (also, see Table 4). The amplified PCR products were digested with ApaI enzyme and ligated together at the common ApaI site. These ligated DNAs were used as template to PCR amplify each of the Hcap constructs using primers 13-101.pr1 (SEQ ID NO: 37) and 13-101.pr4 (SEQ ID NO: 38), which flank the 5' and 3 'regions of each helper, respectively. The amplified Hcap helper DNAs were used to transcribe RNA in vitro for use in VRP packaging experiments.

TABLE 4

Primers for Hcap construct cloning.

| Primer name | Primer sequence 5'-3' | Region amplified |
|---|---|---|
| 13-101.pr1 | CCGGGAAAACAGCATTCCAGGTATTAGA (SEQ ID NO: 37) | Hcap forward |
| 13-101.pr4 | TTTTTTTTTTTTTTTTTTTTTTTTTTTTTTTTTTT TTTTTTTTGAAATATTAAAAACAAAATCCGAT TCGG (SEQ ID NO: 38) | VEE 3' reverse |
| 48-132.pr2 | GACGGGCCCCTTGCCCTTCGTAGCGACAC (SEQ ID NO: 39) | Hcap-1 reverse |
| 48-132.pr4 | GACGGGCCCAGTTTCCAGGTCAGGGTCGC (SEQ ID NO: 40) | Hcap-2 reverse |
| 48-132.pr6 | GACGGGCCCCCTTCATTTTCTTGTCCAATTCCT (SEQ ID NO: 41) | Hcap-3 reverse |
| 48-132.pr8 | GACGGGCCCTGCATACTTATACAATCTGTCCG GA (SEQ ID NO: 42) | Hcap-4 reverse |
| 48-132.pr10 | GACGGGCCCCGGACAGATACAATGATACTTGT GCT (SEQ ID NO: 43) | Hcap-5 reverse |

TABLE 4-continued Primers for Hcap construct cloning.

| Primer name | Primer sequence 5'-3' | Region amplified |
|---|---|---|
| 48-132.pr12 | GACGGGCCCGCCAGATGCGAAAACGCTCTG (SEQ ID NO: 44) | Hcap-6 reverse |
| 48-132.pr14 | GACGGGCCCGCCAGATGCGAAAACGCTCTG (SEQ ID NO: 45) | Hcap-7 reverse |
| 48-132.pr16 | GACGGGCCCTACCTCAAACTGCGGGAAGC (SEQ ID NO: 46) | Hcap-8 reverse |
| 48-132.pr18 | GACGGGCCCTTTTGGGTAGGTAATTGGTCTGG (SEQ ID NO: 47) | Hcap-9 reverse |
| 48-132.pr1 | GACGGGCCCCTATAACTCTCTAC (SEQ ID NO: 48) | Capsid forward |
| 3-8pr4 | GCAACGCGGGGAGGCAGACA (SEQ ID NO: 49) | Capsid reverse |

(b) Plasmid Construction of Selected Truncated Helpers

To construct plasmid versions of selected Hcap clones, each 5' UTR was PCR amplified as described above, digested with EcoRI and ApaI restriction enzymes, and then ligated into a standard VEE replicon vector (see Example 2), which was also digested with EcoRI and ApaI restriction enzymes. The resulting "empty" helper vectors (Δ-helpers) each contained one of the nine deleted 5' UTR regions. The capsid gene was then PCR amplified from a standard capsid helper plasmid with primers 48-132.pr1 and 3-8pr4, as described above, digested with ApaI and NotI restriction enzymes and ligated into each of the Δ-helpers also linearized with ApaI and NotI enzymes.

B. Analysis of Truncated Helper Constructs

Each of the truncated helper constructs was tested separately for its ability to package replicon RNA expressing an immunogen (e.g. the Gag protein from HIV) into VRPs. 30 ug of each of the 3 RNAs (i.e. the truncated capsid helper, standard VEE Gp helper, and an HIV-Gag-expressing replicon RNA) were electroporated into CHO or VERO cells.

1. IFA Analysis of Electroporated CHO Cells

TABLE 5

IFA Analysis of Electroporated CHO Cells

| Sample | GAG | capsid | Gp |
|---|---|---|---|
| Hcap1 | >90% | 20% | >90% |
| Hcap2 | >90% | 15% | >90% |
| Hcap3 | >90% | 15% | >90% |
| Hcap4 | >90% | 10% | >90% |
| Hcap5 | >90% | 5% | >90% |
| Hcap6 | >90% | 5% | >90% |
| Hcap7 | >90% | 5% | >90% |
| Hcap8 | >90% | <1% | >90% |
| Hcap9 | >90% | <1% | >90% |
| Hcap10 | >90% | >90% | >90% |

2. Packaging/recombination analysis in CHO Cells

Packaging/recombination studies were carried out on VRP generated in CHO cells (Table 6). The titer of the resultant GAG VRP and capsid expressing particles was determined by infection of fresh cells and performing IFA for GAG or capsid protein.

High titered VRP (>1×10^8/ml) were generated in CHO cells using Hcap-1 through Hcap-6. Most CHO cell VRP preparations generated with these Hcap RNAs had 20 to >100 fold reduction in capsid copackaging/recombination titer, as compared with Hcap10 (the standard, "full length 5'UTR" capsid helper).

TABLE 6

| Sample | GAG VRP Titer/ml | capsid titer/ml | fold reduction capsid titer vs hcap10 |
|---|---|---|---|
| Hcap1 | $2.5 \times 10^8$ | $1.4 \times 10^3$ | 23.6 |
| Hcap2 | $1.0 \times 10^8$ | $1.4 \times 10^3$ | 23.6 |
| Hcap3 | $1.8 \times 10^8$ | $7.1 \times 10^2$ | 46.5 |
| Hcap4 | $1.4 \times 10^8$ | $2.6 \times 10^2$ | 126.9 |
| Hcap5 | $1.1 \times 10^8$ | $1.4 \times 10^3$ | 23.6 |
| Hcap6 | $1.7 \times 10^8$ | $6.7 \times 10^3$ | 4.9 |
| Hcap7 | $8.8 \times 10^7$ | $1.4 \times 10^3$ | 23.6 |
| Hcap8 | $2.8 \times 10^6$ | nd | nd |
| Hcap9 | $7.4 \times 10^6$ | $3.5 \times 10^2$ | 94.3 |
| Hcap10 | $3.4 \times 10^8$ | $3.3 \times 10^4$ | 0.0 | nd: not determined

3. Packaging/Recombination Analysis in Vero Cells using Selected Helpers

Plasmid clones were prepared for the truncated 5' UTRs of Hcap1 through Hcap4, and the clones were sequenced to confirm their identity. Using the Hcap4 truncated helper to provide the capsid protein, VRP were produced following co-electroporation into Vero cells with an HIV-Gag VEE replicon RNA and a standard Gp RNA helper. (see Example 2).

IFA analysis of Vero cells infected with these VRP at an MOI of ~50-100 (to ensure 100% infection of cells) was carried out 16 hr post infection using an anti-capsid antibody. The number of cells that were IFA-positive for capsid was determined per field at a 10× magnification, and this number was used to calculate a copackaging-recombination titer for capsid on a per milliliter basis. Table 7 provides the results using this truncated helper, as compared with the standard capsid helper ("Hcap10").

TABLE 7

VRP and Capsid titers in Vero cells using Hcap4 Helper

| Sample | GAG VRP Titer/ml | capsid titer/ml | fold reduction capsid titer vs hcap10 |
|---|---|---|---|
| Hcap4 | $9.6 \times 10^8$ | $1.3 \times 10^4$ | 36.2 |
| Hcap10 | $1.2 \times 10^9$ | $4.7 \times 10^5$ | 0.0 |

Example 4

T7 Polymerase-Driven Helpers

A. T7 Polymerase-Driven VEE Glycoprotein Helper

The glycoprotein (Gp) genes from the Gp helper are amplified by PCR and cloned downstream from an EMC IRES. The EMC/Gp fragment is then cloned into pCRBlunt (Invitrogen, Carlsbad, Calif.) under the control of a T7 RNA polymerase promoter. Transfection of this pCRBlunt-EMC/Gp DNA (Fugene 6, Boehringer Mannheim, Indianapolis, Ind.) into BHK-21 cells expressing T7 RNA polymerase protein resulted in VEE Gp protein expression in cells transfected with the DNA, as determined by IFA.

B. Resolving T7-Polymerase Driven VEE DNA Helper

Construction of VEE DNA Resolving Helper

The VEE capsid protein is amplified from standard C helper plasmid (see Example 2) using the VEECapF/XbaI primer (SEQ ID NO: 23) and the VEECapR/BamHI primer (SEQ ID NO: 24) (also, see Table 8). The resulting PCR product is cloned into pCR4-TOPO (InVitrogen Corp., Carlsbad, Calif.), resulting in pC4-Vcapsid, and orientation is verified by restriction enzyme analysis with SpeI. The VEE glycoprotein genes are PCR amplified from the standard Gp helper plasmid using the VEEGpTEP/BamHI primer (containing the 21nt sequence encoding the tobacco etch virus protease recognition sequence (TEP); SEQ ID NO: 25) and the VEEGpR/EcoRV primer (SEQ ID NO: 26) (also, see Table 8) followed by restriction enzyme digest with BamHI. The pCR4-VCapsid clone is digested with BamHI and PmeI and ligated with the Bam HI-digested VEEGp PCR product to generate a structural protein coding cassette with the protease recognition sequence in between the capsid and Gp sequences. The EMCV IRES is PCR amplified from pIRES using EMCV-2 forward (SEQ ID NO: 17) and reverse (SEQ ID NO: 18) primers, digested with NheI and cloned into the XbaI restriction enzyme site of pCR4-VSp, and orientation is verified by PCR analysis with EMCV-2 forward and VEE-CapR/BamHI.

TABLE 8

Primers for T7 promoter driven DNA Resolving Helper

| Primer | Primer Sequence |
|---|---|
| VEECapF/ XbaI | 5'-GTCTAGAATGTTCCCGTTCCAACCAATG-3' (SEQ ID NO: 23) |
| VEECapR/ BamHI | 5'-CGGGATCCCCATTGCTCGCAGTTCTCCGG-3' (SEQ ID NO: 24) |
| VEEGpTEP/ BamHI | 5'-CGGGATCCGAAAACCTGTATTTTCAGGGCATGTCACT AGTGACCACCATGTGTCTGCTCGCC-3' (SEQ ID NO: 25) |

TABLE 8-continued

Primers for T7 promoter driven DNA Resolving Helper

| Primer | Primer Sequence |
|---|---|
| VEEGpR/ EcoRV | 5'-CGATATCTCAATTATGTTTCTGGTTG-3' (SEQ ID NO: 26) |

Example 5

Pol II Promoter-driven Non-replicating Helpers

A. Construction of Helpers

Alphavirus structural protein genes are PCR amplified using gene specific primers that possess unique restriction enzyme sites and cloned downstream of a DNA Polymerase II promoter for gene expression in transfected cells. In the case of VEE constructs, capsid and/or Gp genes were PCR amplified from the C-helper or Gp-helper and cloned into pCDNA-3.1 (InVitrogen, Carlsbad, Calif.) under the control of a CMV promoter. None of the clones retained any VEE 5'UTR, 3'UTR or 26S RNA sequences. The following constructs were generated:

| Name: | Expression Product: |
|---|---|
| pCDNA-VCap | VEE capsid protein |
| pCDNA-VcapCleave | VEE capsid protein and 8 amino acids of the E3 protein |
| pCDNA-VGp(X/X/N) | VEE Gps |
| pCDNA-VSp | VEE capsid protein and Gps (all VEE structural proteins) |

To construct pCDNA-VSp, the VEE glycoprotein gene was PCR amplified from the standard Gp helper plasmid (see Example 2) using the VEEGpF/XbaI primer (SEQ ID NO: 27) and the VEEGpR/NheI primer (SEQ ID NO: 28) (also, see Table 9). The resulting PCR product was digested with XbaI and NheI restriction enzymes and cloned into the XbaI site of pCDNA3.1(−) to generate pCDNA-VGp(X/N). Orientation with respect to the CMV immediate early promoter was verified by restriction enzyme analysis with XbaI and SpeI. The full-length VEE capsid gene was PCR amplified from the standard C helper plasmid (see Example 2) using the VEE-CapF/XbaI primer (SEQ ID NO: 29) and the 3-42pr4 primers (SEQ ID NO: 30) (also, see Table 9). This PCR product was digested with XbaI and ligated into pCDNA-VGp(X/N) at the XbaI restriction enzyme site to generate pCDNA-VSp. Orientation was verified by restriction enzyme analysis with SpeI.

TABLE 9

Primers for constructing pCDNA-VSp

| Primer | Sequence |
|---|---|
| VEEGpF/XbaI | 5'-GTCTAGAATGTCCCTAGTGACCACCATG-3' (SEQ ID NO: 27) |
| VEEGpR/NheI | 5'-GCGCTAGCGTCAATTATGTTTCTGGTTG-3' (SEQ ID NO: 28) |

TABLE 9-continued

Primers for constructing pCDNA-VSp

| Primer | Sequence |
|---|---|
| VEECapF/XbaI | 5'-GTCTAGAATGTTCCCGTTCCAACCAATG-3' (SEQ ID NO: 29) |
| 3-42pr4 | 5'-CAATCGCCGCGAGTTCTATG-3' (SEQ ID NO: 30) |

B. Transfection with pCDNA-VSp 293T cells in T-175 flasks were transfected with 20 μg pCDNA-VSp DNA using Fugene® 6 (Roche, Indianapolis, Ind.) or Lipofectamine® 2000 (LF2K; Gibco-BRL, Gaithersburg, Md.) and cells were incubated for 6 or 24 h at 37° C. with 5% $CO_2$. Cells were trypsinized, washed twice in PBS and resuspended at $1.2 \times 10^7$ cells/ml in 800 μl PBS. Cells were then mixed with 30 μg of an alphavirus replicon RNA encoding GFP and transferred to a 0.4 cm gap electroporation cuvette. The cells and RNA were pulsed three times at 450 V and 25 μF. After 10 minutes at room temperature, the cells were seeded into T75 flasks with 25 mls DMEM+10% FBS. Samples of each electroporation were aliquoted to 96 well plates for immunofluorescence analysis and all cells were incubated at 37° C. with 5% $CO_2$.

At approximately 16 h post-electroporation, cells in 96 well plates were fixed with 2% formaldehyde; 0.2% gluteraldehyde and analyzed for GFP protein expression. Samples were alternatively fixed with MeOH and analyzed by IFA for VEE capsid and Gp protein expression. Results are summarized in Table 10, as a percentage of the electroporated cells expressing protein.

TABLE 10

Percentage of cells expressing protein 16 h after electroporation.

| Helper | Time* | GFP | VEE Capsid | VEE Gp |
|---|---|---|---|---|
| Cap/Gp RNA | 6 h | 50% | 50% | 50% |
| Cap/Gp RNA | 24 h | 80% | >50% | >50% |
| VSp (Fugene) | 6 h | 80% | <1% | 1% |
| VSp (Fugene) | 24 h | >80% | <1% | 30% |
| VSp (LF2K) | 6 h | 80% | 10% | 50% |
| VSp (LF2K) | 24 h | >80% | 1% | 80% |

*Time elapsed following transformation with helpers that cells were harvested for electroporation with GFP-replicon RNA Western analysis demonstrates the presence and proper processing of the capsid protein in cells transformed with pCDNA-VSp.

C. GFP-expressing VRP Production using DNA Helpers

Each of the constructs described in (A.) were tested separately or in combination for their ability to package replicon particles expressing a reporter (e.g. GFP protein).

1. 293T Cells 293T cells transformed with DNA constructs were electroporated with 30 ug GFP-expressing RNA. 30 ug of Capsid or Gp helper RNAs were included in electroporation of cells receiving only Gp or Capsid DNAs respectively. At approximately 24 h after replicon RNA electroporation as described in (B.), the culture medium was harvested and cell debris was removed by centrifugation in a swinging bucket rotor for 5 min. at 2000 rpm. The supernatant was transferred to new 50 ml conical tubes and stored at 4° C. Ten-fold serial dilutions of clarified culture medium, containing alphavirus GFP-VRPs, were prepared, and 30 μl of each dilution were inoculated onto Vero cells in 96-well plates. Cells were incubated overnight at 37° C. with 5% $CO_2$ followed by fixation in 2% formaldehyde/0.2% glutaraldehyde. Titrations were determined by counting the number of cells that were GFP positive in 5 fields at the lowest possible dilution. Results are summarized in Table 11 below:

TABLE 11

GFP VRP Production using DNA Helpers.

| Sample | Titer/ml VRP | IFA for GFP* | IFA for Capsid* | IFA for Gp* |
|---|---|---|---|---|
| Control** | $1.5 \times 10^6$ | >80% | 20% | 20% |
| VCap | $6.4 \times 10^4$ | 50% | 20% | 10% |
| CapCleave | $1.0 \times 10^5$ | 50% | 20% | 10% |
| VGp(X/X/N) | $4.3 \times 10^4$ | 50% | 20% | 20% |
| VSp | $1.9 \times 10^5$ | 50% | 1% | 30% |
| CapCleave + VGp (X/X/N) | $4.3 \times 10^4$ | 50% | 20% | 20% |

*Percent of electroporated cells positive for GFP, Capsid or Gp protein expression.
**(Controls = GFP replicon particles generated using VEE Capsid and Gp helper RNAs)

2. Optimization of DNA Transfection in 293T Cells Followed by Electroporation using pCDNA-VSp At approximately 24 h after replicon RNA electroporation as described in (B.), the culture medium was harvested and cell debris was removed by centrifugation in a swinging bucket rotor for 5 min. at 2000 rpm. The supernatant was transferred to new 50 ml conical tubes and stored at 4° C. Ten-fold serial dilutions of clarified culture medium, containing alphavirus GFP-VRPs, were prepared, and 30 μl of each dilution were inoculated onto Vero cells in 96-well plates. Cells were incubated overnight at 37° C. with 5% $CO_2$ followed by fixation in 2% formaldehyde/0.2% glutaraldehyde. Titrations were determined by counting the number of cells that were GFP positive in 5 fields at the lowest possible dilution. Results are summarized in Table 12.

TABLE 12

VRP titers generated using pCDNA-VSp helper

| Helper | Time* | Titer (VRP/ml) |
|---|---|---|
| Cap/Gp RNA | 6 h | $1.49 \times 10^7$ |
| Cap/Gp RNA | 24 h | $5.69 \times 10^7$ |
| VSp (Fugene) | 6 h | $2.13 \times 10^5$ |
| VSp (Fugene) | 24 h | $2.13 \times 10^6$ |
| VSp (LF2K) | 6 h | $9.26 \times 10^5$ |
| VSp (LF2K) | 24 h | $2.85 \times 10^6$ |

*Time after transformation with helpers that cells were harvested for subsequent electroporation with GFP replicon RNA D. HIV-Gag Expressing VRP Production using pCDNA-VSp Helper 293T cells in T175 flasks were transfected with pCDNA-VSp DNA, as above, collected 6 h later, and then electroporated with 30 μg HIV-Gag replicon RNA (see Olmsted, et al., WO 02/03917). Electroporated cells were seeded into T75 flasks and samples were aliquotted into 96-well plates. At 16 h post-electroporation, samples of the helper cells in 96-well plates were fixed in methanol and analyzed by IFA for HIV-Gag, VEE Capsid or VEE Gp protein expression.

Culture medium containing the VRPs released from electroporated cells was collected, and titrations to determine recombinant alphavirus particle yield were measured. Titers for HIV-Gag expressing VRP, as well as Capsid and Gp copackaging/single recombinants, were determined by IFA (Table 13).

TABLE 13

GAG VRP titers and copackaging with VSp DNA helpers.

| Helper | HIV-Gag (VRP/ml) | Capsid (FFU/ml) | Gp (FFU/ml) |
|---|---|---|---|
| Cap/Gp RNA | $7.75 \times 10^6$ | $1.03 \times 10^3$ | $1.42 \times 10^3$ |
| pCDNA-VSp | $1.64 \times 10^6$ | none detected | none detected |

The results in Table 13 demonstrate that the HIV-Gag VRP titers from the pCDNA-VSp helper were less then 10-fold lower than titers obtained with the bipartite RNA helper system ("Cap/Gp RNA") while the packaging/recombination frequencies were decreased by at least three orders of magnitude.

Example 6

Construction of Resolving DNA Helpers

A. Resolving DNA Helper A

To construct this embodiment of the invention, alphavirus capsid and glycoprotein structural protein genes are cloned into two separate positions in the single helper DNA molecule. At least one structural gene, located in the first position, is cloned directly downstream from a DNA dependant RNA polymerase II (pol II) promoter. One or more structural genes, not encoded in the first position, are located in the second position, being positioned downstream of the first position, such that the transcript resulting from the pol II promoter-directed expression contains an IRES element directly 5' to the structural protein gene(s) in the downstream position.

One method of construction employs first PCR amplifying the selected alphavirus capsid or glycoprotein structural proteins using structural-gene specific primers that also code for unique restriction enzyme sites. The sequence encoding the structural protein gene(s) located in the first position is cloned directly into the DNA dependent RNA polymerase II (pol II) promoter-based expression vector of choice. The sequence encoding the structural protein gene(s) located in the second position is initially cloned into a transfer vector that contains an IRES sequence such that the transcript eventually resulting from the promoter-directed expression will contain an IRES element directly 5' to the structural protein gene(s) coding sequence in the second position.

To insert the ribozyme sequence, overlapping complementary primers that encode a ribozyme are annealed to produce a ribozyme linker sequence with unique 5' and 3' restriction sites at each end. Then, the IRES-structural protein gene fragment is digested out of the transfer vector, and the pol II expression vector is digested at the unique 3' restriction site of the sequence encoding the gene(s) in the first position and at another unique restriction site further downstream that is compatible with the 3' site of the IRES-structural protein gene DNA fragment. The construct is completed by ligating the IRES-structural protein gene fragment and the pol II expression vector together at the compatible 5' and 3' sites at the ends of the ribozyme linker sequence.

Construction of a VEE Helper A

The VEE glycoprotein (GP) gene is amplified with GP forward (SEQ ID NO: 1) and GP reverse primers (SEQ ID NO: 2) (also, see Table 1) and the VEE capsid (C) gene is amplified with C forward (SEQ ID NO: 5) and C reverse primers (SEQ ID NO: 6) (also, see Table 1) using GP-helper and C-helper plasmids as templates for PCR, respectively (e.g. Pushko et al, 1997). The VEE GP PCR product is digested with NheI and ApaI restriction enzymes and ligated into a suitable vector linearized with the same restriction enzymes and containing a polII promoter, such as the commercially available pCDNA3.1 (Invitrogen, Carlsbad, Calif.; note that this vector, as well as other commercially available vectors, is engineered with a selectable marker for use of the purchased plasmid in mammalian cell culture, but since the claimed inventions do not require such a marker, it is removed prior to insertion of the VEE structural protein coding sequence(s)). In employing pCDNA3.1, the VEE GP gene is then located downstream of the CMV immediate early (IE) promoter, generating pCDNA3.1/sp1.

The VEE capsid PCR fragment is digested with XbaI and SalI restriction enzymes and ligated into a suitable vector linearized with the same restriction enzymes and containing as IRES, such as the commercially available XbaI/SalI linearized pIRES DNA (Clontech, Palo Alto, Calif.). This manipulation generates pIRES/sp2. Overlapping complementary primers hdR-Forward (SEQ ID NO: 7) and hdR-Reverse (SEQ ID NO: 8) (also, see Table 1), coding for the hepatitis delta ribozyme (hdR), are annealed together to generate an hdR linker sequence with ApaI and XhoI restriction sites at the 5' and 3' ends, respectively. The vector portion of the construct is produced by digesting pCDNA3.1/sp1 with ApaI and NotI restriction enzymes. A 1502 base pair XhoI/NotI IRES/sp2 fragment digested from pIRES/sp2 DNA and the ApaI/XhoI hdR linker fragment are then ligated with ApaI/NotI linearized pCDNA3.1/sp1 to generate VEE Helper A.

B. Resolving DNA Helpers B and C

To construct other embodiments of the invention, an alphavirus structural protein helper vector (e.g. comprising an alphaviral 5' replication recognition sequence, either an alphavirus transcriptional promoter (herein Helper B; e.g. an 26S alphavirus subgenomic promoter) or an internal ribosome entry site (IRES) (herein Helper C; e.g. the EMCV IRES), a nucleic acid sequence encoding the upstream alphavirus structural protein gene(s), and an alphavirus 3' replication recognition sequence) is cloned directly into a polII promoter-based expression vector of choice (see Example 5). Concomitantly, the nucleic acid sequence encoding the alphavirus structural protein gene(s) in the downstream fragment is cloned into a transfer vector containing an IRES sequence, as described herein. To assemble Helper B, the IRES-structural protein coding sequence fragment is then digested out of the transfer vector and the released fragment is ligated into the promoter expression vector, so that the polII promoter directs the expression of the structural proteins in both the upstream and downstream positions.

Helper C is prepared in two steps from Helper B. The first step is to remove the 26S promoter from Helper B, while introducing a unique restriction site in its place. The second step is to clone an IRES sequence into the unique engineered restriction site.

Construction of a VEE Helper B.

The CMV IE promoter is PCR amplified from pIRES2-DsRed2 (Clontech) using the CMV forward primer (SEQ ID NO: 9) and the CMV reverse primer (SEQ ID NO: 10) (also, see Table 1). The VEE 5' non-coding region, 26S promoter, GP gene and VEE 3' noncoding region is amplified from a GP-helper plasmid (see Example 4A) using the GP-2 forward primer (SEQ ID NO: 3) and the GP-2 reverse primer (SEQ ID NO: 4) (also, see Table 1). The CMV IE PCR product and the GP-helper PCR product have a 53 nt region of homology at their 3' and 5'ends, respectively. This region of homology allows an overlapping PCR reaction to produce a gene construct containing the CMV IE promoter that initiates transcription at the VEE 5' end of the GP-helper sequence. The CMV IE/GP-helper fragment is then digested with NheI restriction enzyme. The pol II promoter-based vector pCDNA3.1 is linearized with BglII restriction enzyme and then treated with T4 DNA polymerase to produce a blunt end. The vector is further digested with NheI to release the existing CMV IE and T7 RNA polymerase promoters from the vector. The NheI digested CMV IE/GP-helper PCR product is then ligated into the BglII(T4 treated)/NheI digested pCDNA3.1 vector, generating pCDNA3.1/sp1.2. The 1502 base pair XhoI/NotI IRES/sp2 fragment digested from pIRES/sp2 DNA and the ApaI/XhoI hdR linker fragment are then ligated with ApaI/NotI linearized pCDNA3.1/sp1.2 to generate VEE Helper B.

Construction of VEE Helper C.

Removal of the 26S promoter in Helper B is accomplished by PCR, using two sets of primers. The first set of primers (d26S forward (SEQ ID NO: 11) and d26S reverse (SEQ ID NO: 12); also, see Table 1) amplify a fragment containing the CMV IE and the VEE 5' non-coding region (NCR). The d26S reverse primer anneals upstream from the 26S promoter so that it is not included in the PCR product. The CMV IE/VEE 5' NCR PCR product encodes a 5' PvuI site, found in the backbone of Helper B DNA, and an engineered unique AscI restriction site at the 3' end of the VEE 5' NCR. The second set of primers (E3 forward (SEQ ID NO: 13) and 6K reverse (SEQ ID NO: 14); also, see Table 1) amplify a product containing the VEE E3-6K region of the GP-helper that also does not contain the 26S promoter. The E3-6K product contains an engineered 5' AscI site and a 3' unique SgrAI restriction site found in the 6K gene. After PCR amplification, the CMV IE/VEE 5' NCR PCR product is digested with PvuI and AscI restriction enzymes, and the E3-6K product is digested with AscI and SgrAI restriction enzymes. Helper B DNA (see above) is digested with PvuI and SgrAI restriction enzymes to release the CMV IE-VEE 5' NCR-26S-E3-6K region. A new Helper is then reconstituted by ligating the PvuI/AscI CMV IE/VEE 5' NCR digested fragment and the AscI/SgrAI E3-6K digested fragment with the PvuI/SgrAI digested Helper B vector, generating Helper B.2. Helper B.2 is identical to Helper B except that the 26S promoter has been removed and a unique AscI restriction site has replaced it.

The EMCV IRES is amplified from the pIRES vector using the EMCV forward primer (SEQ ID NO: 15) and the EMCV reverse primer (SEQ ID NO: 16) which both contain engineered 5' AscI restriction sites (also, see Table 1). After amplification, the EMCV IRES PCR product is digested with AscI restriction enzyme and ligated into AscI linearized Helper B.2 DNA, generating Helper C.

C. Resolving DNA Helper D

Another embodiment of this invention can be constructed by modifying Helper A to contain an IRES element that directs cap-independent translation of the alphavirus structural proteins in the upstream as well as the downstream location, a construct referred to herein as Helper D.

Construction of a VEE Helper D.

The EMCV IRES is amplified from the pIRES vector using the EMCV-2 forward primer (SEQ ID NO: 17) and the EMCV-2 reverse primer (SEQ ID NO: 18), each containing engineered 5' NheI restriction sites (also, see Table 1). After amplification, the EMCV IRES PCR product is digested with NheI restriction enzyme and ligated into NheI linearized VEE Helper A, generating VEE Helper D.

Example 7

Chimeric Alphavirus RNA Helpers

A. Construction of VEE-SIN Helper

The VEE capsid gene was cloned into the XbaI restriction site of the pSINrep5 replicon vector (InVitrogen, Carlsbad, Calif.). Sindbis-based helpers that contain the VEE capsid gene were constructed by deleting portions of the Sindbis nsP region from the pSINrep5/VEEcapsid construct. The pΔSIN/VEEcapsid DNA was prepared by digesting pSINrep5/VEE-capsid DNA with SmaI and BamHI restriction enzymes, deleting 6567 base pairs (bp) of the nsP genes. A second helper construct (pΔSIN/VEEcap-2), lacking an additional 667 bp of the nsP region, was prepared by PCR amplifying a region of pΔSIN/VEEcapsid, using the primers ΔSIN26S/RsrII forward (SEQ ID NO: 31) and ΔSIN-ApaI/reverse (SEQ ID NO: 32) (also, see Table 14) and ligating it into RsrII and ApaI linearized pΔSIN/VEEcapsid DNA.

TABLE 14

| PCR primers used to generate ΔSIN/VEEcap-2 | | |
|---|---|---|
| primer | Sequence 5'-3' | Region amplified |
| ΔSIN26S/ RsrII forward | TTTCGGACCGTCTCTACGGTGGTCCTAAAT AGTC (SEQ ID NO: 31) | nsP and VEE capsid |
| ΔSIN-ApaI/ reverse | CTGGTCGGATCATTGGGCCC (SEQ ID NO: 32) | nsP and VEE capsid |

B. HIV-Gag Expressing VRP Production using a Chimeric Alphavirus Helper

The ΔSIN/VEEcapsid or ΔSIN/VEEcap-2 helpers were used to generate VRP in Vero cells with a VEE Gp RNA helper (as described herein) and a VEE RNA replicon expressing the HIV Gag gene. The culture medium containing HIV-Gag VRP, generated using either the ΔSIN/VEE-capsid or ΔSIN/VEEcap-2 helper, was collected, and the yield of VRPs was determined using an HIV-Gag IFA. Using the ΔSIN/VEEcapsid helper, a VRP titer of $2.6 \times 10^6$/ml was obtained; using the ΔSIN/VEEcap-2 helper, a VRP titer of $1.9 \times 10^6$/ml was obtained.

Example 8

Construction of Nodavirus-based Helper RNAs

Generally, the constructs are produced as follows. The alphavirus capsid gene is PCR amplified with gene specific primers that introduce restriction enzyme sites. The PCR amplified product is cloned directly into a Nodavirus RNA2 (generated from either flock house virus (FHV) or nodamura (NoV)), which are digested with compatible restriction enzymes.

Construction of Nodavirus VEE Capsid Helpers

The VEE capsid gene is PCR amplified with the capsid F (MluI) primer (SEQ ID NO: 19) and the capsid R (MluI) primer (SEQ ID NO: 20) that introduce a MluI site, (also, see Table 1), using pCDNA VSp (see Example 5) as the template. The VEE capsid PCR product is digested with MluI and ligated into the MluI digested FHV RNA2 vector and the BssHII digested NoV RNA2. BssHII digestion produces compatible cohesive ends with MluI. The resultant clones are sequenced to determine orientation and to verify sequence accuracy.

Alternatively, the VEE capsid gene can be directionally cloned into the NcoI and MluI sites of FHV RNA2 and the NcoI and BssHII sites of NoV RNA2. This NcoI site is 5' to the MluI or BssHII sites in the FHV and NoV RNA2, respectively, separated by one nucleotide. The VEE capsid gene is PCR amplified with one of two forward primers containing an NcoI site, capsid F1 (NcoI) (SEQ ID NO: 21) and capsid F2 (NcoI) (SEQ ID NO: 22), and a reverse primer that contains a MluI site, capsid R (MluI) (SEQ ID NO: 20), using pCDNA VSp (see Example 5) as the template. The resultant VEE capsid 1 and VEE capsid 2 PCR products are digested with NcoI and MluI and ligated into the NcoI/MluI digested FHV RNA2 vector and the NcoI/BssHII digested NoV RNA2 vector.

In addition, the VEE glycoprotein gene and the entire VEE structural protein gene cassette can be cloned into the FHV RNA2 and the NoV RNA2 expression vectors as described above using appropriate primers.

The nodavirus capsid helper described herein is co-electroporated into VERO cells at 28 C with nodavirus RNA1, a VEE GP helper (e.g. see Pushko, et. al. 1997, ibid.) and a VEE RNA replicon expressing the HIV gag protein (see Olmsted et al., WO 02/03917). When the FHV RNA 1 and 2 are used, recombinant alphavirus particle yields were $4.3 \times 10^6$ per ml. When the NoV RNA 1 and 2 are used, particle yields were approximately $2 \times 10^5$ per ml.

Example 9

Production of Replicon Particles using DNA or RNA Helpers

The replicon RNA and helper nucleic acids can be introduced to the helper cell by one or more of several different techniques generally known to the art, e.g. electroporation, transfection (e.g. using calcium phosphate precipitation or nucleic acids deposited on microbeads or nanoparticles), lipid-mediated DNA uptake, micro- or nano-projectiles, stable transformation, by incorporation into a viral vector, such as adenovirus, SV40, poxvirus (e.g. modified vaccinia Ankara), nodavirus or adenoassociated virus, or by coating onto a virus vector, such as adenovirus. When using a combination of DNA helper nucleic acids and an RNA replicon, these molecules may be introduced at different times using different techniques. The difference in timing may provide a period of time for recovery by the cells, and it may also allow optimization of the differing kinetics of expression from a DNA vector as compared with an RNA vector. The timing can be 30 minutes, 1, 2, 3, 4, 5, 6, 7, 8, 9, 10, 11, 12, or 24 hours between the introduction of each nucleic acid molecule to the cells. The introduction of DNA helper(s) by a different means and prior to the electroporation of replicon RNA (and helper RNA, as appropriate) does not have significant detrimental effects on the efficiency of the RNA electroporation.

Transfection of DNA Helpers

Lipid-Mediated

293T, VERO or DF1 cells are first transfected with the DNA helper by lipofection using Fugene® 6 (Boehringer Mannheim, Indianapolis, Ind.). Cells are incubated in the presence of Fugene and DNA in medium containing 10% FBS for 1 to 24 hours. After incubation, they are washed with PBS and collected by trypsinization.

Electroporation

Transfection of DNA into Vero cells using commercially available cationic lipids such as FuGene and Lipofectamine is typically inefficient (~1% efficiency). While these methods may be sufficient for certain applications, electroporation of DNA helpers into Vero cells is a preferred alternative approach. Various parameters of the electroporation process can be optimized to enhance the efficiency of DNA entry into Vero cells.

For example, it is preferable to use purified DNA constructs. For example, plasmid DNA containing a gene under the control of a CMV promoter is first isolated using a high purity maxiprep system (e.g. Qiagen®; Promega Corporation, Madison, Wis.). Such initially purifed DNA is preferably further purified by phenol extraction in the presence of ethidium bromide and high salt (reference: Stemmer, W P, *Biotechniques*. 1991 June; 10(6):726). This further purified DNA is resuspended in nuclease free water prior to electroporation.

Another optimization step involves the culturing conditions for Vero cells can be optimized for electroporation of DNA. Vero cells are initially cultured in EMEM medium and grown to late log phase, then harvested by trypsinization, washed twice with Invitrus® (Cell Culture Technologies GmBh, Zurich, Switzerland), and resuspended in 800 µl Invitrus medium.

These Invitrus-bathed cells are combined with an optimized amount of purified DNA (typically, concentrations range from 10 µg to 200 µg) and then transferred to a 0.4 cm² gap cuvette. Electroporations is performed using a Biorad Gene Pulser® (BioRad Laboratories, Inc., Hercules, Calif.), with four pulses at 50 µF, over a range of voltages (500-700V). After electroporation, the Vero cells were seeded into 6 well plates and incubated for 24 hours at 37° C. with 5% $CO_2$.

In determining the optimized parameters, expression of protein is first analyzed at 16 and 23 hours post-electroporation. The percentage of transfected cells, varying the above parameters, ranged from 1%-40%; an example of an optimized set of parameters is: 150 µg purified plasmid DNA and pulsing four times at 650V, 50 µF. In addition, there is typically an additional 5-10% increase in expression between 17 and 23 hours post-electroporation.

Electroporation efficiency can also be enhanced by synchronizing the Vero cells in a specific phase of the cell cycle. In one example, cells are synchronized in the G2/M phase with aphidicolin (1 mg/ml) prior to electroporation (see Golzio, M, Biochem Biophys Acta. 2002 June 13:1563(1-2): 23-8). These synchronized cells are handled as described above and combined with 50 µg of plasmid DNA prior to electroporation. In this example, aphidicolin-treated cells show a two-fold increase in the percentage of cells transfected, as compared to untreated (unsynchronized) cells.

Electroporation of Alphavirus Replicon RNA

After introduction of the DNA helpers of this invention, $1.2 \times 10^7$ cells are then electroporated in the presence of a replicon RNA and appropriate helper RNAs (if required) under the following conditions: 450V (293T) or 850V (VERO and DF1) and 25 uF in 0.4 cm gap electroporation cuvettes (pulse 3×'s with 4 sec. between pulses). Electroporated cells are then allowed to recover for 10 min. before seeding into 25 mls medium containing 10% FBS.

When using RNA replicon and RNA helper combinations, all RNAs may be co-electroporated into the helper cell at the same time. Methods for RNA electroporation are as described above. In an alternative embodiment, when introducing the DNA helpers to the helper cell via electroporation, the replicon RNA may be co-electroporated with the DNA helpers.

```
                              SEQUENCE LISTING

<160> NUMBER OF SEQ ID NOS: 49

<210> SEQ ID NO 1
<211> LENGTH: 31
<212> TYPE: DNA
<213> ORGANISM: Artificial Sequence
<220> FEATURE:
<223> OTHER INFORMATION: Description of Artificial Sequence; NOTE =
      Synthetic Construct

<400> SEQUENCE: 1
ctagctagct atgtcactag tgaccaccat g                                   31

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence; NOTE =
      Synthetic Construct

<400> SEQUENCE: 2
gggccctcaa ttatgtttct ggttggt                                        27

<210> SEQ ID NO 3
<211> LENGTH: 53
<212> TYPE: DNA
<213> ORGANISM: Artificial Sequence
<220> FEATURE:
<223> OTHER INFORMATION: Description of Artificial Sequence; NOTE =
      Synthetic Construct

<400> SEQUENCE: 3
gcagagctgg tttagtgaac cgtataggcg gcgcatgaga gaagcccaga cca           53

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence; NOTE =
      Synthetic Construct

<400> SEQUENCE: 4
gctagcgctc ttccctttt tttttt                                          26

<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence; NOTE =
      Synthetic Construct

<400> SEQUENCE: 5
gctctagaat gttcccgttc cagccaatg                                      29

<210> SEQ ID NO 6
<211> LENGTH: 52
<212> TYPE: DNA
<213> ORGANISM: Artificial Sequence
```

```
<220> FEATURE:
<223> OTHER INFORMATION: Description of Artificial Sequence; NOTE =
      Synthetic Construct

<400> SEQUENCE: 6
gcgtcgacgt cttggccata gcggccgcgg ttacagacac atggtggtca ct            52

<210> SEQ ID NO 7
<211> LENGTH: 91
<212> TYPE: DNA
<213> ORGANISM: Artificial Sequence
<220> FEATURE:
<223> OTHER INFORMATION: Description of Artificial Sequence; NOTE =
      Synthetic Construct

<400> SEQUENCE: 7
cgggtcggca tggcatctcc acctcctcgc ggtccgacct gggcatccga aggaggacgt    60
cgtccactcg gatggctaag ggagagctcg c                                   91

<210> SEQ ID NO 8
<211> LENGTH: 99
<212> TYPE: DNA
<213> ORGANISM: Artificial Sequence
<220> FEATURE:
<223> OTHER INFORMATION: Description of Artificial Sequence; NOTE =
      Synthetic Construct

<400> SEQUENCE: 8
tcgagcgagc tctcccttag ccatccgagt ggacgacgtc ctccttcgga tgcccaggtc    60
ggaccgcgag gaggtggaga tgccatgccg acccgggcc                           99

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence; NOTE =
      Synthetic Construct

<400> SEQUENCE: 9
tagttattaa tagtaatcaa ttacgg                                         26

<210> SEQ ID NO 10
<211> LENGTH: 53
<212> TYPE: DNA
<213> ORGANISM: Artificial Sequence
<220> FEATURE:
<223> OTHER INFORMATION: Description of Artificial Sequence; NOTE =
      Synthetic Construct

<400> SEQUENCE: 10
tggtctgggc ttctctcatg cgccgcctat acggttcact aaaccagctc tgc           53

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence; NOTE =
      Synthetic Construct

<400> SEQUENCE: 11
ggcgcgccgt cctccgatcg ttgtcagaag                                     30
```

```
<210> SEQ ID NO 12
<211> LENGTH: 36
<212> TYPE: DNA
<213> ORGANISM: Artificial Sequence
<220> FEATURE:
<223> OTHER INFORMATION: Description of Artificial Sequence; NOTE =
      Synthetic Construct

<400> SEQUENCE: 12
ggcgcgcctc cgtcaaccgc gtatacatcc tggtaa                           36

<210> SEQ ID NO 13
<211> LENGTH: 31
<212> TYPE: DNA
<213> ORGANISM: Artificial Sequence
<220> FEATURE:
<223> OTHER INFORMATION: Description of Artificial Sequence; NOTE =
      Synthetic Construct

<400> SEQUENCE: 13
ggcgcgccat gtcactagtg accaccatgt g                                31

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence; NOTE =
      Synthetic Construct

<400> SEQUENCE: 14
ctcgtaggcg ccggcgcctg cgg                                         23

<210> SEQ ID NO 15
<211> LENGTH: 29
<212> TYPE: DNA
<213> ORGANISM: Artificial Sequence
<220> FEATURE:
<223> OTHER INFORMATION: Description of Artificial Sequence; NOTE =
      Synthetic Construct

<400> SEQUENCE: 15
ggcgcgccaa ttccgcccct ctccctccc                                   29

<210> SEQ ID NO 16
<211> LENGTH: 29
<212> TYPE: DNA
<213> ORGANISM: Artificial Sequence
<220> FEATURE:
<223> OTHER INFORMATION: Description of Artificial Sequence; NOTE =
      Synthetic Construct

<400> SEQUENCE: 16
ggcgcgcctt atcatcgtgt ttttcaaag                                   29

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence; NOTE =
      Synthetic Construct

<400> SEQUENCE: 17
gctagcaatt ccgcccctct ccctccc                                     27
```

```
<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence; NOTE =
      Synthetic Construct

<400> SEQUENCE: 18
gctagcttat catcgtgttt ttcaaag                                          27

<210> SEQ ID NO 19
<211> LENGTH: 29
<212> TYPE: DNA
<213> ORGANISM: Artificial Sequence
<220> FEATURE:
<223> OTHER INFORMATION: Description of Artificial Sequence; NOTE =
      Synthetic Construct

<400> SEQUENCE: 19
cgacgcgtat gttcccgttc cagccaatg                                        29

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence; NOTE =
      Synthetic Construct

<400> SEQUENCE: 20
gcacgcgttt acagacacat ggtggtcact                                       30

<210> SEQ ID NO 21
<211> LENGTH: 36
<212> TYPE: DNA
<213> ORGANISM: Artificial Sequence
<220> FEATURE:
<223> OTHER INFORMATION: Description of Artificial Sequence; NOTE =
      Synthetic Construct

<400> SEQUENCE: 21
cctgccatgg tataaatgtt cccgttccaa ccaatg                                36

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence; NOTE =
      Synthetic Construct

<400> SEQUENCE: 22
cctgccatgg ccccgttcca accaatg                                          27

<210> SEQ ID NO 23
<211> LENGTH: 28
<212> TYPE: DNA
<213> ORGANISM: Artificial Sequence
<220> FEATURE:
<223> OTHER INFORMATION: Description of Artificial Sequence; NOTE =
      Synthetic Construct

<400> SEQUENCE: 23
gtctagaatg ttcccgttcc aaccaatg                                         28
```

```
<210> SEQ ID NO 24
<211> LENGTH: 29
<212> TYPE: DNA
<213> ORGANISM: Artificial Sequence
<220> FEATURE:
<223> OTHER INFORMATION: Description of Artificial Sequence; NOTE =
      Synthetic Construct

<400> SEQUENCE: 24
cgggatcccc attgctcgca gttctccgg                                           29

<210> SEQ ID NO 25
<211> LENGTH: 62
<212> TYPE: DNA
<213> ORGANISM: Artificial Sequence
<220> FEATURE:
<223> OTHER INFORMATION: Description of Artificial Sequence; NOTE =
      Synthetic Construct

<400> SEQUENCE: 25
cgggatccga aaacctgtat tttcagggca tgtcactagt gaccaccatg tgtctgctcg         60
cc                                                                        62

<210> SEQ ID NO 26
<211> LENGTH: 26
<212> TYPE: DNA
<213> ORGANISM: Artificial Sequence
<220> FEATURE:
<223> OTHER INFORMATION: Description of Artificial Sequence; NOTE =
      Synthetic Construct

<400> SEQUENCE: 26
cgatatctca attatgtttc tggttg                                              26

<210> SEQ ID NO 27
<211> LENGTH: 28
<212> TYPE: DNA
<213> ORGANISM: Artificial Sequence
<220> FEATURE:
<223> OTHER INFORMATION: Description of Artificial Sequence; NOTE =
      Synthetic Construct

<400> SEQUENCE: 27
gtctagaatg tccctagtga ccaccatg                                            28

<210> SEQ ID NO 28
<211> LENGTH: 28
<212> TYPE: DNA
<213> ORGANISM: Artificial Sequence
<220> FEATURE:
<223> OTHER INFORMATION: Description of Artificial Sequence; NOTE =
      Synthetic Construct

<400> SEQUENCE: 28
gcgctagcgt caattatgtt tctggttg                                            28

<210> SEQ ID NO 29
<211> LENGTH: 28
<212> TYPE: DNA
<213> ORGANISM: Artificial Sequence
<220> FEATURE:
<223> OTHER INFORMATION: Description of Artificial Sequence; NOTE =
      Synthetic Construct

<400> SEQUENCE: 29
gtctagaatg ttcccgttcc aaccaatg                                            28
```

```
<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence; NOTE =
      Synthetic Construct

<400> SEQUENCE: 30
caatcgccgc gagttctatg                                              20

<210> SEQ ID NO 31
<211> LENGTH: 34
<212> TYPE: DNA
<213> ORGANISM: Artificial Sequence
<220> FEATURE:
<223> OTHER INFORMATION: Description of Artificial Sequence; NOTE =
      Synthetic Construct

<400> SEQUENCE: 31
tttcggaccg tctctacggt ggtcctaaat agtc                              34

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence; NOTE =
      Synthetic Construct

<400> SEQUENCE: 32
ctggtcggat cattgggccc                                              20

<210> SEQ ID NO 33
<211> LENGTH: 35
<212> TYPE: DNA
<213> ORGANISM: Artificial Sequence
<220> FEATURE:
<223> OTHER INFORMATION: Description of Artificial Sequence; NOTE =
      Synthetic Construct

<400> SEQUENCE: 33
cgggatccat gcggtttgat gcgggtgcat acatc                             35

<210> SEQ ID NO 34
<211> LENGTH: 31
<212> TYPE: DNA
<213> ORGANISM: Artificial Sequence
<220> FEATURE:
<223> OTHER INFORMATION: Description of Artificial Sequence; NOTE =
      Synthetic Construct

<400> SEQUENCE: 34
gctctagatt agccgtagag agttataggg g                                 31

<210> SEQ ID NO 35
<211> LENGTH: 30
<212> TYPE: DNA
<213> ORGANISM: Artificial Sequence
<220> FEATURE:
<223> OTHER INFORMATION: Description of Artificial Sequence; NOTE =
      Synthetic Construct

<400> SEQUENCE: 35
tggcgcgccg ctcggaattc cccctctccc                                   30
```

<210> SEQ ID NO 36
<211> LENGTH: 29
<212> TYPE: DNA
<213> ORGANISM: Artificial Sequence
<220> FEATURE:
<223> OTHER INFORMATION: Description of Artificial Sequence; NOTE = Synthetic Construct

<400> SEQUENCE: 36
aggcgcgcct tctatgtaag cagcttgcc                             29

<210> SEQ ID NO 37
<211> LENGTH: 28
<212> TYPE: DNA
<213> ORGANISM: Artificial Sequence
<220> FEATURE:
<223> OTHER INFORMATION: Description of Artificial Sequence; NOTE = Synthetic Construct

<400> SEQUENCE: 37
ccgggaaaac agcattccag gtattaga                              28

<210> SEQ ID NO 38
<211> LENGTH: 73
<212> TYPE: DNA
<213> ORGANISM: Artificial Sequence
<220> FEATURE:
<223> OTHER INFORMATION: Description of Artificial Sequence; NOTE = Synthetic Construct

<400> SEQUENCE: 38
tttttttttt tttttttttt tttttttttt tttttttttt ttttgaaat attaaaaaca    60 aaatccgatt cgg                                              73

<210> SEQ ID NO 39
<211> LENGTH: 29
<212> TYPE: DNA
<213> ORGANISM: Artificial Sequence
<220> FEATURE:
<223> OTHER INFORMATION: Description of Artificial Sequence; NOTE = Synthetic Construct

<400> SEQUENCE: 39
gacgggcccc ttgcccttcg tagcgacac                             29

<210> SEQ ID NO 40
<211> LENGTH: 29
<212> TYPE: DNA
<213> ORGANISM: Artificial Sequence
<220> FEATURE:
<223> OTHER INFORMATION: Description of Artificial Sequence; NOTE = Synthetic Construct

<400> SEQUENCE: 40
gacgggccca gtttccaggt cagggtcgc                             29

<210> SEQ ID NO 41
<211> LENGTH: 33
<212> TYPE: DNA
<213> ORGANISM: Artificial Sequence
<220> FEATURE:
<223> OTHER INFORMATION: Description of Artificial Sequence; NOTE = Synthetic Construct

<400> SEQUENCE: 41
gacgggcccc cttcattttc ttgtccaatt cct                        33

<210> SEQ ID NO 42
<211> LENGTH: 34
<212> TYPE: DNA
<213> ORGANISM: Artificial Sequence
<220> FEATURE:
<223> OTHER INFORMATION: Description of Artificial Sequence; NOTE = Synthetic Construct

<400> SEQUENCE: 42
gacgggccct gcatacttat acaatctgtc cgga                             34

<210> SEQ ID NO 43
<211> LENGTH: 35
<212> TYPE: DNA
<213> ORGANISM: Artificial Sequence
<220> FEATURE:
<223> OTHER INFORMATION: Description of Artificial Sequence; NOTE = Synthetic Construct

<400> SEQUENCE: 43
gacgggcccc ggacagatac aatgatactt gtgct                            35

<210> SEQ ID NO 44
<211> LENGTH: 30
<212> TYPE: DNA
<213> ORGANISM: Artificial Sequence
<220> FEATURE:
<223> OTHER INFORMATION: Description of Artificial Sequence; NOTE = Synthetic Construct

<400> SEQUENCE: 44
gacgggcccg ccagatgcga aaacgctctg                                  30

<210> SEQ ID NO 45
<211> LENGTH: 30
<212> TYPE: DNA
<213> ORGANISM: Artificial Sequence
<220> FEATURE:
<223> OTHER INFORMATION: Description of Artificial Sequence; NOTE = Synthetic Construct

<400> SEQUENCE: 45
gacgggcccg ccagatgcga aaacgctctg                                  30

<210> SEQ ID NO 46
<211> LENGTH: 29
<212> TYPE: DNA
<213> ORGANISM: Artificial Sequence
<220> FEATURE:
<223> OTHER INFORMATION: Description of Artificial Sequence; NOTE = Synthetic Construct

<400> SEQUENCE: 46
gacgggccct acctcaaact gcgggaagc                                   29

<210> SEQ ID NO 47
<211> LENGTH: 32
<212> TYPE: DNA
<213> ORGANISM: Artificial Sequence
<220> FEATURE:
<223> OTHER INFORMATION: Description of Artificial Sequence; NOTE = Synthetic Construct

<400> SEQUENCE: 47
gacgggccct tttgggtagg taattggtct gg                               32

-continued

```
<210> SEQ ID NO 48
<211> LENGTH: 23
<212> TYPE: DNA
<213> ORGANISM: Artificial Sequence
<220> FEATURE:
<223> OTHER INFORMATION: Description of Artificial Sequence; NOTE =
      Synthetic Construct

<400> SEQUENCE: 48
gacgggcccc tataactctc tac                                              23

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence; NOTE =
      Synthetic Construct

<400> SEQUENCE: 49
gcaacgcggg gaggcagaca                                                  20
```

What is claimed is:

1. A recombinant replicon nucleic acid comprising, in order:

(i) a nucleotide sequence encoding a 5' alphavirus replication recognition sequence;

(ii) a nucleotide sequence encoding alphavirus nonstructural proteins nsp1, nsp2 and nsp3;

(iii) a nucleotide sequence selected from the group consisting of a transcriptional promoter and an internal ribosome entry sequence (IRES);

(iv) a nucleotide sequence encoding at least one heterologous nucleic acid of interest;

(v) an internal ribosome entry sequence;

(vi) a nucleotide sequence encoding alphavirus nonstructural protein nsp4; and (vii) a nucleotide sequence encoding a 3' alphavirus replication recognition sequence.

2. The recombinant replicon nucleic acid of claim 1 wherein the nucleic acid is RNA.

3. A cDNA molecule encoding the recombinant replicon nucleic acid of claim 2.

4. The recombinant replicon nucleic acid of claim 1, wherein the nucleotide sequences of (i), (ii), (vi) and (vii) are derived from the group of alphaviruses consisting of Venezuelan equine encephalitis virus, Semliki Forest virus, Sindbis virus, Ross River virus and S.A.AR86 virus.

5. An alphavirus vector construct comprising a 5' promoter operably linked to the cDNA of claim 3.

6. The recombinant replicon nucleic acid of claim 1, wherein the nucleotide sequence of (iii) is a transcriptional promoter.

7. The recombinant replicon nucleic acid of claim 1, wherein the nucleotide sequence of (iii) is an internal ribosome entry sequence.

8. The recombinant replicon nucleic acid of claim 6, wherein the transcriptional promoter is an alphavirus 26S promoter.

9. A vector comprising the recombinant replicon nucleic acid of claim 1.

10. A isolated cell comprising the vector of claim 9.

11. A helper cell comprising the recombinant replicon nucleic acid of claim 1.

12. The helper cell of claim 11, further comprising a recombinant DNA molecule comprising a promoter for directing the transcription of RNA from a DNA sequence operably linked to a nucleotide sequence comprising a complete alphavirus structural polyprotein-coding sequence.

13. The helper cell of claim 11, further comprising a first helper RNA encoding at least one but not all alphavirus structural proteins and a second helper RNA encoding any alphavirus structural proteins not encoded by the first helper RNA.

14. The helper cell of claim 13, wherein the alphavirus structural proteins are selected from the group consisting of VEE, Sindbis, S.A.AR 86, Semliki Forest virus and Ross River virus structural proteins.

15. The helper cell of claim 12, wherein the alphavirus structural polyprotein-coding sequence comprises one or more attenuating mutations.

16. The helper cell of claim 13, wherein one or more of the helper RNAs encode one or more alphavirus structural proteins comprising one or more attenuating mutations.

17. The helper cell of claim 11, wherein the recombinant replicon nucleic acid molecule is electroporated into the helper cell.

18. The helper cell of claim 12, wherein the recombinant DNA molecule is electroporated into the helper cell.

19. The helper cell of claim 13, wherein the helper RNA molecules are electroporated into the helper cell.

20. An infectious defective alphavirus particle comprising the recombinant replicon nucleic acid of claim 2.

21. A composition comprising a population of infectious, defective, alphavirus replicon particles, comprising the recombinant replicon nucleic acid of claim 2, wherein the population has no detectable replication-competent virus, as measured by passage on cell culture.

22. The composition of claim 21, wherein the alphavirus replicon particles comprise alphavirus structural proteins comprising one or more attenuating mutations.

23. The composition of claim 21, wherein the recombinant replicon nucleic acid is derived from the group of alphaviruses consisting of Venezuelan equine encephalitis virus, Semliki Forest virus, Sindbis virus, Ross River virus and S.A.AR86 virus.

24. The composition of claim 21, wherein the alphavirus replicon particles comprise alphavirus structural proteins selected from the group consisting of VEE, Sindbis, S.A.AR 86, Semliki Forest virus and Ross River virus structural proteins.

25. A method of making infectious, defective alphavirus particles, comprising introducing recombinant replicon nucleic acid of claim 1 into a helper cell under conditions whereby infectious, defective alphavirus particles are produced in the helper cell.

26. The method of claim 25, wherein the helper cell comprises a recombinant DNA molecule comprising a promoter for directing the transcription of RNA from a DNA sequence operably linked to a nucleotide sequence comprising a complete alphavirus structural polyprotein-coding sequence.

27. The method of claim 25, wherein the helper cell comprises a first helper RNA encoding at least one but not all alphavirus structural proteins and a second helper RNA encoding any alphavirus structural proteins not encoded by the first helper RNA.

28. The method of claim 26, wherein the alphavirus structural proteins are selected from the group consisting of VEE, Sindbis, S.A.AR 86, Semliki Forest virus and Ross River virus structural proteins.

29. The method of claim 27, wherein the alphavirus structural proteins are selected from the group consisting of VEE, Sindbis, S.A.AR 86, Semliki Forest virus and Ross River virus structural proteins.

30. The method of claim 27, wherein the alphavirus structural proteins comprise one or more attenuating mutations.

31. The method of claim 25, wherein the recombinant replicon nucleic acid molecule is electroporated into the helper cell.

32. The method of claim 26, wherein the recombinant DNA molecule is electroporated into the helper cell.

33. The method of claim 27, wherein the helper RNA molecules are electroporated into the helper cell.

34. An infectious defective alphavirus particle produced by the method of claim 25.

* * * * *

UNITED STATES PATENT AND TRADEMARK OFFICE
CERTIFICATE OF CORRECTION

PATENT NO.      : 7,425,337 B2
APPLICATION NO. : 11/376901
DATED           : September 16, 2008
INVENTOR(S)     : Smith et al.

It is certified that error appears in the above-identified patent and that said Letters Patent is hereby corrected as shown below:

Column 39, Line 1 under the Sequence Listing,
          Please correct: "<160> NUMBER OF SEQ ID NOS: 49"
          To read: --<160> NUMBER OF SEQ ID NOS: 51--

Column 55, Line 25, please add to the Sequence Listing after SEQ ID NO: 49 as follows <210> 50
<211> 7
<212> PRT
<213> Unknown <220>
<223> TEV protease recognition sequence

<400> 50

Glu Asn Leu Tyr Phe Gln Gly
1               5

<210> 51
<211> 5
<212> PRT
<213> Unknown

<220>
<223> TuMV recognition sequence

UNITED STATES PATENT AND TRADEMARK OFFICE
CERTIFICATE OF CORRECTION

PATENT NO.           : 7,425,337 B2
APPLICATION NO.  : 11/376901
DATED                    : September 16, 2008
INVENTOR(S)          : Smith et al.

It is certified that error appears in the above-identified patent and that said Letters Patent is hereby corrected as shown below:

<220>
<221> MISC_FEATURE
<222> (1)..(1)
<223> Xaa can be any aliphatic amino acid

<400> 51

Xaa Val Arg His Gln
1           5

Column 55, Claim 10:
            Please correct: "A isolated cell comprising the vector of claim 9."
            To read: --An isolated cell comprising the vector of claim 9.--

Signed and Sealed this

Twenty-seventh Day of January, 2009

JOHN DOLL
*Acting Director of the United States Patent and Trademark Office*